(12) United States Patent
Park et al.

(10) Patent No.: US 7,658,715 B2
(45) Date of Patent: Feb. 9, 2010

(54) MINIATURE ACTUATOR MECHANISM FOR INTRAVASCULAR IMAGING

(75) Inventors: Byong-Ho Park, Cincinnati, OH (US); Stephen M. Rudy, Palo Alto, CA (US)

(73) Assignee: Fluid Medical, Mountain View, CA (US)

( * ) Notice: Subject to any disclaimer, the term of this patent is extended or adjusted under 35 U.S.C. 154(b) by 499 days.

(21) Appl. No.: 11/415,855

(22) Filed: May 2, 2006

(65) Prior Publication Data

US 2007/0016063 A1  Jan. 18, 2007

Related U.S. Application Data

(60) Provisional application No. 60/678,676, filed on May 4, 2005, provisional application No. 60/677,944, filed on May 4, 2005, provisional application No. 60/710,304, filed on Aug. 22, 2005, provisional application No. 60/711,653, filed on Aug. 25, 2005, provisional application No. 60/781,786, filed on Mar. 13, 2006.

(51) Int. Cl.
*A61B 8/14* (2006.01)
(52) U.S. Cl. .................. 600/463; 600/462; 600/466; 600/467; 600/459; 600/437
(58) Field of Classification Search .......... 600/459, 600/462, 463
See application file for complete search history.

(56) References Cited

U.S. PATENT DOCUMENTS

| | | | |
|---|---|---|---|
| 4,794,931 A | 1/1989 | Yock | |
| 4,887,605 A | 12/1989 | Angelsen et al. | |
| 5,000,185 A | 3/1991 | Yock | |
| 5,203,337 A * | 4/1993 | Feldman | 600/463 |
| 5,238,005 A | 8/1993 | Imran | |
| 5,271,402 A * | 12/1993 | Yeung et al. | 600/437 |
| 5,349,964 A | 9/1994 | Imran | |
| 5,373,845 A | 12/1994 | Gardineer et al. | |
| 5,373,849 A | 12/1994 | Maroney et al. | |

(Continued)

FOREIGN PATENT DOCUMENTS

DE  42 38 176 A1  5/1994

(Continued)

OTHER PUBLICATIONS

International Preliminary Report on Patentability issued on Dec. 11, 2007 in PCT/US2006/033408, filed Aug. 24, 2006.

(Continued)

*Primary Examiner*—Long V Le
*Assistant Examiner*—Nigel Fontenot
(74) *Attorney, Agent, or Firm*—Knobbe Martens Olson & Bear LLP

(57) ABSTRACT

The present invention relates to a new intravascular imaging device based on a Shape Memory Alloy (SMA) actuator mechanism embedded inside an elongate member such as a guide wire or catheter. The present invention utilizes a novel SMA mechanism to provide side-looking imaging by providing movement for an ultrasound transducer element. This novel SMA actuator mechanism can be easily fabricated in micro-scale, providing an advantage over existing imaging devices because it offers the ability to miniaturize the overall size of the device, while the use of multiple transducer crystals maximizes field of view. Also disclosed are methods of using the same.

34 Claims, 9 Drawing Sheets

U.S. PATENT DOCUMENTS

| | | | |
|---|---|---|---|
| 5,377,685 A | 1/1995 | Kazi et al. | |
| 5,379,772 A | 1/1995 | Imran | |
| 5,383,923 A | 1/1995 | Webster, Jr. | |
| 5,409,000 A | 4/1995 | Imran | |
| 5,409,453 A | 4/1995 | Lundquist et al. | |
| 5,478,330 A | 12/1995 | Imran et al. | |
| 5,482,029 A | 1/1996 | Sekiguchi et al. | |
| 5,549,542 A | 8/1996 | Kovalcheck | |
| 5,606,975 A * | 3/1997 | Liang et al. | 600/462 |
| 5,779,688 A | 7/1998 | Imran et al. | |
| 5,813,997 A | 9/1998 | Imran et al. | |
| 5,844,140 A * | 12/1998 | Seale | 73/633 |
| 5,853,368 A | 12/1998 | Solomon et al. | |
| 5,873,906 A | 2/1999 | Lau et al. | |
| 5,938,623 A | 8/1999 | Quiachon et al. | |
| 5,938,671 A | 8/1999 | Katoh et al. | |
| 5,968,064 A | 10/1999 | Selmon et al. | |
| 6,004,330 A | 12/1999 | Middleman et al. | |
| 6,068,638 A | 5/2000 | Makower | |
| 6,110,121 A | 8/2000 | Lenker | |
| 6,157,852 A | 12/2000 | Selmon et al. | |
| 6,200,269 B1 | 3/2001 | Lin et al. | |
| 6,235,000 B1 | 5/2001 | Milo et al. | |
| 6,241,667 B1 | 6/2001 | Vetter et al. | |
| 6,241,744 B1 | 6/2001 | Imran et al. | |
| 6,296,615 B1 | 10/2001 | Brockway | |
| 6,306,097 B1 | 10/2001 | Park et al. | |
| 6,500,147 B2 | 12/2002 | Omaleki et al. | |
| 6,501,551 B1 | 12/2002 | Tearney | |
| 6,547,803 B2 | 4/2003 | Seward et al. | |
| 6,572,551 B1 | 6/2003 | Smith et al. | |
| 6,592,526 B1 | 7/2003 | Lenker | |
| 6,599,304 B1 | 7/2003 | Selmon et al. | |
| 6,749,560 B1 | 6/2004 | Konstorum et al. | |
| 2002/0072669 A1 | 6/2002 | Masters | |
| 2004/0056751 A1 * | 3/2004 | Park et al. | 337/139 |
| 2004/0254471 A1 | 12/2004 | Hadjicostis et al. | |

FOREIGN PATENT DOCUMENTS

| | | |
|---|---|---|
| WO | WO 97/23865 A | 7/1997 |
| WO | WO 98/46119 A | 10/1998 |
| WO | WO 99/40963 A | 8/1999 |
| WO | WO 2004/096049 A2 | 11/2004 |

OTHER PUBLICATIONS

International Preliminary Report on Patentability issued on Jun. 20, 2007 in PCT/US2006/017130, filed May 2, 2006.

International Search Report and Written Opinion issued on Aug. 28, 2006 in PCT/US2006/016599, filed May 2, 2006.

International Search Report and Written Opinion issued on Dec. 1, 2006 in PCT/US2006/017130, filed May 2, 2006.

International Search Report and Written Opinion issued on Jun. 12, 2007 in PCT/US2006/033408, filed Aug. 24, 2006.

Office Action issued on Dec. 24, 2008 in U.S. Appl. No. 11/415,848, filed on May 2, 2006.

* cited by examiner

1200a

1201b

1201a

1292

1291

1200b

MINIATURE ACTUATOR MECHANISM FOR INTRAVASCULAR IMAGING

CROSS-REFERENCE TO RELATED APPLICATIONS

This Application claims priority under 35 U.S.C. 119 to U.S. Provisional Application Ser. No. 60/678,676, filed May 4, 2005, titled "Multiple transducers for large field of view in intravascular ultrasound imaging," U.S. Provisional Application Ser. No. 60/677,944, filed May 4, 2005, titled "Shape memory alloy (SMA) mechanism for side-looking intravascular imaging," U.S. Provisional Application Ser. No. 60/710,304, filed Aug. 22, 2005, titled "Guide wire enabled with intravascular ultrasound imaging for interventional applications," and U.S. Provisional Application Ser. No. 60/711,653, filed Aug. 25, 2005, titled "Miniature mirror-based intravascular ultrasound imaging device for interventional applications," and U.S. Provisional Application Ser. No. 60/781,786, filed Mar. 13, 2006, titled "Electrically driven miniature intravascular optical coherence tomography imaging device," the entire contents of each of which are incorporated herein by reference. This application is also related to U.S. patent application Ser. No. 11/415,848 filed on May 2, 2006, entitled "MULTIPLE TRANSDUCERS FOR INTRAVASCULAR ULTRASOUND IMAGING" and U.S. patent application Ser. No. 11/416,402 filed on May 2, 2006, entitled "MINIATURE ACTUATOR MECHANISM FOR INTRAVASCULAR OPTICAL IMAGING," the entire contents of each of which are incorporated herein by reference.

BACKGROUND OF THE INVENTION

1. Field of the Invention

The present invention concerns a miniature actuator which is useful in intravascular imaging devices including intravascular ultrasound (IVUS), and optical coherence tomography (OCT). The miniature actuator mechanism and ultrasound or OCT imaging device is embedded in an elongate member such as an intravascular guide wire or catheter to provide imaging guidance in various interventional applications. Also disclosed is a reflector-based ultrasound imaging device created to minimize the overall scale of the imaging device, as well as ultrasound transducers having multiple transducer crystals to increase the field of view of the device while maintaining its small size.

2. Description of the Related Art

Coronary artery disease is very serious and often requires an emergency operation to save lives. The main cause of coronary artery disease is the accumulation of plaques inside artery, which eventually occludes blood vessels. Several solutions are available, e.g., balloon angioplasty, rotational atherectomy, and intravascular stents, to open up the clogged section, which is called stenosis. Traditionally, during the operation, surgeons rely on X-ray fluoroscopic images that are basically planary images showing the external shape of the silhouette of the lumen of blood vessels. Unfortunately, with X-ray fluoroscopic images, there is a great deal of uncertainty about the exact extent and orientation of the atherosclerotic lesions responsible for the occlusion, making it difficult to find the exact location of the stenosis. In addition, though it is known that restenosis can occur at the same place, it is difficult to check the condition inside the vessels after surgery. Similarly, intravascular imaging would prove valuable during interventional procedures as an aid to navigation and for intraoperative feedback. For example, the precise placement and appropriate expansion of stents would benefit from concurrent intravascular imaging. Existing intravascular imaging devices are too large and insufficiently flexible to be placed simultaneously with other devices.

In order to resolve these issues, an ultrasonic transducer device has been utilized for endovascular intervention to visualize the inside of the blood vessels. To date, the current technology is mostly based on one or more stationary ultrasound transducers or rotating a single transducer in parallel to the blood vessels by means of a rotating shaft which extends through the length of the catheter to a motor or other rotary device located outside the patient. These devices have limitations in incorporating other interventional devices into a combination device for therapeutic aspects. They require a large space inside catheter such that there is not enough room to accommodate other interventional devices. Also due to the nature of the rotating shaft, the distal end of the catheter is very stiff and it is hard to go through tortuous arteries. The high speed rotating shaft also contributes to distorted non-uniform images when imaging a tortuous path in the vasculature. OCT has also been utilized to visualize the intravascular space based on differential reflectance, but like the existing ultrasound devices, most rely on a rotating fiber optic which extends along the length of the device. This approach also has problems, including for example the manipulation, spinning and scanning motion required with respect to a delicate glass or polycarbonate optical fiber; the actuator mechanism located outside the patient and tip located inside the patient are significantly distant from one another, leading to inefficiencies and control issues arising from the torque created by a long, spinning member; and remote mechanical manipulation and a long spinning element distort the image due to non-uniform rotational distortion. Given the numerous difficulties with current intravascular imaging devices, there is a need for improved intravascular imaging devices.

SUMMARY OF THE INVENTION

One embodiment of the invention is a side-looking intravascular ultrasound apparatus comprising an elongate member having a proximal end and a distal end, where at least a portion of the distal end is at least transparent to ultrasound energy; an actuator mechanism disposed in the distal end, the actuator mechanism comprising a first anchor, a second anchor, at least one movable element, a first SMA actuator connected to the first anchor and a movable element, and a deformable component connected to the second anchor and at least one movable element, where the anchor elements are secured relative to the elongate member; and an ultrasound transducer connected to the movable element, the transducer oriented to transmit ultrasound energy through the ultrasound transparent portion of the distal end at an angle of between about 15° to about 165° relative to a longitudinal axis of the elongate member; where the first SMA actuator has an activated and a deactivated state; and where the movable element and transducer move in a first direction relative to the elongate member upon activation of the first SMA actuator. In another embodiment of the apparatus, the deformable component comprises a second SMA actuator; where the second actuator has an activated and a deactivated state; and where activation of the second SMA actuator following deactivation of the first SMA actuator moves the movable element and transducer relative to the elongate member in a second direction of movement which is counter to the first direction of movement. In yet another embodiment of the apparatus, the deformable component is elastic or superelastic; where the deformable component has a relaxed state and a deformed state; where the deformable component is in a relaxed state when the first SMA actuator is deactivated; where the movement of the movable element and transducer in the first direction upon activation of the first SMA actuator deforms the elastic or superelastic deformable component; and where following deactivation of the first SMA actuator, the elastic or superelastic deformable component substantially returns to the relaxed state, the movable element and transducer moving in a second direction of movement which is counter to the first direction of movement.

In another embodiment of the apparatus described herein, the first and second direction of movement is rotational about the longitudinal axis of the elongate member, or substantially parallel to the longitudinal axis of the elongate member. In some embodiments, the elongate member is a guide wire. In some embodiments the apparatus further comprises a lumen traversing the longitudinal axis of the elongate member; and wires disposed in the lumen to electrically connect the transducer, first SMA and optionally the deformable component to one or more devices at the proximal end of the elongate member. In some embodiments the device is an ultrasound signal processor. In some embodiments the apparatus further comprises a second ultrasound transducer connected to the movable element. In some embodiments of the apparatus, the angle is between about 80° and about 110°; in some embodiments the diameter of the distal end of the elongate member is not more than about 0.060 inches.

Some embodiments of the apparatus of further comprise a connecting arm, the connecting arm connecting the ultrasound transducer to a movable element; where the movable element, connecting arm and transducer move in a first direction relative to the elongate member upon activation of the first SMA actuator. In some embodiments of the apparatus, the deformable component comprises a second SMA actuator; where the second actuator has an activated and a deactivated state; and where activation of the second SMA actuator following deactivation of the first SMA actuator moves the movable element, connector and transducer relative to the elongate member in a second direction of movement which is counter to the first direction of movement. In some embodiments the deformable component is elastic or superelastic; where the deformable component has a relaxed state and a deformed state; where the deformable component is in a relaxed state when the first SMA actuator is deactivated; where the movement of the movable element, connecting arm and transducer in the first direction upon activation of the first SMA actuator deforms the elastic or superelastic deformable component; and where following deactivation of the first SMA actuator, the elastic or superelastic deformable component substantially returns to the relaxed state, the movable element, connecting arm and transducer moving in a second direction of movement which is counter to the first direction of movement.

In some embodiments, the rotational motion is between about 1 and about 400 degrees, and the longitudinal motion is from about 1 mm to about 20 mm. Some embodiments further comprise a second ultrasound transducer connected to a movable element. In some embodiments, the ultrasound transducer further comprises at least two ultrasound crystals. In some embodiments, the transducer is oriented to transmit ultrasound energy through the ultrasound transparent portion of the distal end at an angle of between about 80° and about 110° relative to a longitudinal axis of the elongate member.

Another embodiment is a side-looking intravascular ultrasound apparatus comprising an elongate member having a proximal end and a distal end, where at least a portion of the distal end is transparent to ultrasound energy; an actuator mechanism disposed in the distal end, the actuator mechanism comprising a first anchor, a second anchor, a movable element, a first SMA actuator connected to the first anchor and the movable element, and a deformable component connected to the second anchor and the movable element, where the anchor elements are secured relative to the elongate member; a connecting arm and an ultrasound energy reflector, where the connecting arm connects the ultrasound energy reflector to a moveable element; and an ultrasound transducer disposed in the distal end of the elongate member; where the ultrasound transducer and the ultrasound energy reflector are oriented to transmit ultrasound energy through the ultrasound transparent portion of the distal end at an angle of between about 15° to about 165° relative to a longitudinal axis of the elongate member; where the first SMA actuator has an activated and a deactivated state; and where the movable element, connecting arm, and ultrasound energy reflector move in a first direction relative to the elongate member upon activation of the first SMA actuator. In some embodiments the deformable component comprises a second SMA actuator; where the second actuator has an activated and a deactivated state; and where activation of the second SMA actuator following deactivation of the first SMA moves the movable element, connecting arm and reflector relative to the elongate member in a second direction which is counter to the first direction of movement. In some embodiments the deformable component is elastic or superelastic; where the deformable component has a relaxed state and a deformed state; where the deformable component is in a relaxed state when the first SMA actuator is deactivated; where the movement of the movable element, connecting arm and reflector in the first direction upon activation of the first SMA actuator deforms the elastic or superelastic deformable component; and where following deactivation of the first SMA actuator, the elastic or superelastic deformable component substantially returns to the relaxed state, the movable element, connecting element and reflector moving in a second direction of movement which is counter to the first direction of movement. Some embodiments further comprise a second ultrasound energy reflector connected to a movable element. In some embodiments, the ultrasound transducer and the ultrasound energy reflector are oriented to transmit ultrasound energy through the ultrasound transparent portion of the distal end at an angle of between about 80° and about 110° relative to a longitudinal axis of the elongate member Also disclosed is a method for visualizing the interior of a patient's vasculature, the method comprising inserting the distal end of an apparatus disclosed herein into the vasculature of a patient; generating an ultrasound signal from the transducer; generating a cyclical movement of the movable element and ultrasound transducer by alternating the activation and deactivation of the first SMA and optionally the deformable component, such that the movable element and ultrasound transducer are moved in the first and the second direction; receiving an ultrasonic signal reflected from the interior of the vasculature on the transducer; and producing an image from the reflected signal. In some embodiments of the method, the cyclical movement of the movable element and ultrasound transducer is generated by alternating the activation of the first SMA and the second SMA such that the movable element and ultrasound transducer are moved in the first and the second direction.

Another embodiment of the method for visualizing the interior of a patient's vasculature comprises inserting the distal end of an apparatus described herein into the vasculature of a patient; generating an ultrasound signal from the transducer; generating a cyclical movement of the movable element, connecting arm and ultrasound transducer by alternating the activation and deactivation of the first SMA and optionally the deformable component, such that the movable element, connecting arm and ultrasound transducer are moved in the first and the second direction; receiving an ultrasonic signal reflected from the interior of the vasculature on the transducer; and producing an image from the reflected signal. In some embodiments of the method, the cyclical movement of the movable element, connecting arm and ultrasound transducer is generated by alternating the activation of the first SMA and the second SMA, such that the movable element, connecting arm and ultrasound transducer are moved in the first and the second direction.

Another embodiment of the method for visualizing the interior of a patient's vasculature comprises inserting the distal end of an apparatus described herein into the vasculature of a patient; generating an ultrasound signal from the transducer; generating a cyclical movement of the movable element, connecting arm and ultrasound energy reflector by alternating the activation of the first SMA and the second SMA, such that the movable element, connecting arm and ultrasound energy reflector are moved in the first and the second direction; receiving an ultrasonic signal reflected from the interior of the vasculature on the transducer; and producing an image from the reflected signal. In some embodiments, the cyclical movement of the movable element, connecting arm and ultrasound energy reflector are generated by alternating the activation of the first SMA and the second SMA, such that the movable element, connecting arm and ultrasound energy reflector are moved in the first and the second direction.

Another embodiment of the apparatus comprises an elongate member having a proximal end and a distal end, where at least a portion of the distal end is transparent to ultrasound energy; an ultrasound transducer disposed in the distal end; and an actuator mechanism means for providing cyclical motion to the transducer disposed in the distal end; where the transducer is oriented to transmit ultrasound energy through the ultrasound transparent portion of the distal end at an angle of between about 15° to about 165° relative to a longitudinal axis of the elongate member. In some embodiments the actuator mechanism means comprises a first anchor, a second anchor, a movable element, a first SMA actuator connected to the first anchor and the movable element, and a deformable component connected to the second anchor and the movable element, where the anchor elements are secured relative to the elongate member.

BRIEF DESCRIPTION OF THE DRAWINGS

FIGS. 2a and 2b are perspective views illustrating rotational motion of the actuator mechanism shown in FIG. 1, while

DETAILED DESCRIPTION OF THE PREFERRED EMBODIMENT

Figure 1:
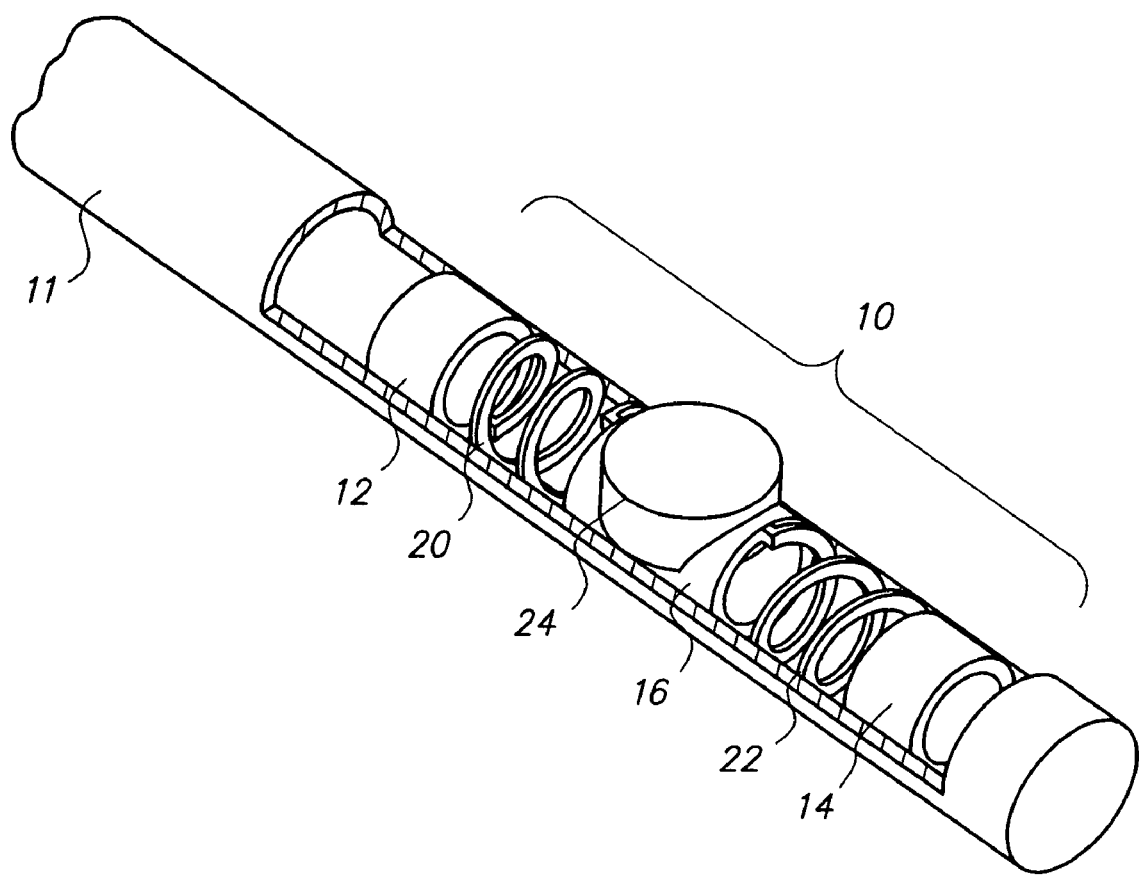
FIG. 1 is a partial cut-away perspective view showing an embodiment of the actuator mechanism of the present invention and an ultrasound transducer disposed in the distal end of an elongate member.

The present invention relates to imaging devices for intravascular imaging, although the present invention is not limited to this preferred application. Imaging of the intravascular space, particularly the interior walls of the vasculature can be accomplished by a number of different means. Two of the most common are the use of ultrasound energy, commonly known as intravascular ultrasound (IVUS) and optical coherence tomography (OCT). Both of these methods are optimized when the instruments (IVUS or OCT) used for imaging a particular portion of the vasculature are repeatedly swept over the area being imaged.

To address the limitations in current devices, a new intravascular imaging device is described based on a Shape Memory Alloy (SMA) actuator mechanism embedded inside an elongate member such as a guide wire or catheter. The present invention utilizes a novel SMA mechanism to provide side-looking imaging by providing movement for an ultrasound transducer or OCT element. Since this novel SMA actuator mechanism can be easily fabricated in micro-scale using laser machining or other fabrication techniques, it provides an advantage over existing imaging devices because it offers the ability to miniaturize the overall size of the device, while the use of multiple transducer crystals maximizes field of view. The small dimensions of the actuator mechanism of the invention allows for the diameter of the elongate member in which it is housed to be very small. The outside diameter of the elongate member, such as a guide wire or catheter containing an imaging device described herein can be as small as from about 0.0050" to about 0.060" outside diameter. The outside diameter for elongate members can be larger when the imaging device is combined with other interventional devices, although the outside diameter of these devices can be as small as 0.060" or smaller. Current catheters containing IVUS range from 0.70 mm to 3 mm in outside diameter.

Because the device does not require a rotating shaft or fiber optic along the length of the catheter, it also allows for a more flexible catheter or guide wire, and provides room for other interventional devices. In addition, it eliminates the problems mentioned above with current OCT technology because it does not require rotating the entire length of the optical fiber. This invention simplifies the manufacture and operation of OCT by allowing a straight fiber optic directed by an independent, oscillating reflector or prism controlled by the actuator mechanism located only in the distal tip of the device. A variation uses the actuator mechanism to rotate only the distal end of the optical fiber, eliminating the need to spin the entire fiber via a remote mechanism.

In a preferred embodiment, an ultrasound reflector can be implemented together with the SMA actuator mechanism. This has an advantage over the prior art because it eliminates the rotational load required to rotate a transducer and accompanying electrical wiring, further reducing size and increasing the amount of movement provided by the actuator, which in turn increases the field of view provided by the device. This preferred embodiment also increases imaging quality by allowing for a thicker backing layer for the ultrasound transducer, since the backing layer does not affect the diameter of the device. This in turn improves the signal-to-noise characteristics of the device and thus improves image quality. In addition, because the transducer does not need to be rotated, this also removes a constraint on the size of the backing layer.

As used herein, elongate member includes any thin, long, flexible structure which can be inserted into the vasculature of a patient. Elongate members include, for example, intravascular catheters and guide wires. The actuator mechanism is disposed in the distal end of the elongate member. As used herein, "distal end" of the elongate member includes any portion of the elongate member from the mid-point to the distal tip. As elongate members can be solid, some will include a housing portion at the distal end for receiving the actuator mechanism. Such housing portions can be tubular structures attached to the side of the distal end or attached to the distal end of the elongate member. Other elongate members are tubular and have one or more lumens in which the actuator mechanism can be housed at the distal end.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used includes methods by which an element is directly secured to another element, such as being glued or otherwise fastened directly to, on, within, etc. another element, as well as indirect means of securing two elements together where one or more elements are disposed between the secured elements.

Movements which are counter are movements in the opposite direction. For example, if the movable element is rotated clockwise, rotation in a counterclockwise direction is a movement which is counter to the clockwise rotation Similarly, if the movable element is moved substantially parallel to the longitudinal axis of the elongate member in a distal direction, movement substantially parallel to the longitudinal axis in a proximal direction is a counter movement.

As used herein, "light" or "light energy" encompasses electromagnetic radiation in the wavelength range including infrared, visible, ultraviolet, and X rays. The preferred range of wavelengths for OCT is from about 400 nm to about 1400 nm. For intravascular applications, the preferred wavelength is about 1200 to about 1400 nm. Optical fibers include fibers of any material which can be used to transmit light energy from one end of the fiber to the other.

"Reflector" as used herein encompasses any material which reflects or refracts a substantial portion of the ultrasound or light energy directed at it. In some embodiments of the OCT device the reflector is a mirror. In others, it is a prism. This allows refractive optical coherence tomography (as opposed to reflective tomography using a mirror.) The prism can also be designed to replace the lens typically required at the distal tip of the optical fiber.

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention can include several novel features, no single one of which is solely responsible for its desirable attributes or which is essential to practicing the inventions herein described.

FIG. 1 illustrates a novel actuator mechanism 10 for achieving the sweeping or scanning motion used for IVUS or OCT imaging. FIG. 1 shows an actuator mechanism 10, which is housed in the distal end of an elongate member 11, with the longitudinal axis of the actuator mechanism 10 oriented substantially parallel to the longitudinal axis of the elongate member 11. The elongate member 11 will be described in greater detail below with reference to FIG. 4. The actuator mechanism 10 includes a first anchor 12 and a second anchor 14 which are secured relative to the interior of the elongate member 11 to anchor the actuator mechanism 10 to the distal end of elongate member 11 such that the anchors 12 and 14 cannot move relative to elongate member 11. The actuator mechanism 10 also has a movable element 16 which is not secured relative to the elongate member 11, and which is free to move in at least one range of motion relative to the anchors 12 and 14 and elongate member 11.

The first anchor 12 is connected to the movable element 16 by a shape memory alloy (SMA) actuator 20 which moves movable element 16 when activated as described in more detail below. The SMA actuator 20 can be fabricated from any known material with shape memory characteristics, the preferred material being nitinol. In an alternative embodiment the actuator mechanism 10 can be fabricated without from a single tubing using any material with shape memory characteristics, incorporating the first anchor 12, second anchor 14, moveable element 16, SMA actuator 20 and deformable component 22 (described below). As known by those of skill in the art, SMAs can be fabricated to take on a predetermined shape when activated. Activation of an SMA actuator consists of heating the SMA such that it adopts its trained shape. Typically, this is accomplished by applying an electric current across the SMA element. Deactivation of an SMA actuator includes turning off current to SMA, such that it returns to its pliable state as it cools. Activation of the SMA to its trained shape results in a force which can be utilized as an actuator. As one of skill in the art will recognize, the disclosed SMA actuator 20 can take numerous shapes and configurations in addition to the helical shape shown in FIG. 1. For example it could be linear, or more than one (e.g. 2, 3, 4 or more) SMA elements could be used to make the SMA actuator 20.

The second anchor 14 is connected to the movable element 16 by a deformable component 22. The deformable component 22 is made from materials which are not rigid, including elastic and superelastic, and non-elastic materials. Deformable materials include trained and untrained SMAs. Elastic alloys include, but are not limited to stainless steel and titanium alloy, and superelastic alloys include but are not limited to, nitinol, Cu—Al—Ni, Cu—Al, Cu—Zn—Al, Ti—V and Ti—Nb alloy.

In an alternative embodiment, one or both of the anchors 12 and 14 are eliminated, and one end the SMA actuator 20 and/or the deformable component 22 are secured directly to the elongate member 11. Also one or both of the anchors 12 and 14 are secured indirectly to the elongate member 11 through additional elements such as an intermediate housing for the actuator mechanism 10. In addition, the SMA actuator 20 and/or deformable component 22 can be connected to either of, or both the anchor 12 or 14 and the movable element 16 through additional elements—they need not be directly connected to the anchor or movable element as shown. Alternatively, the moveable element 16 can include, or have an additional element(s) connected thereto, that extend over or within the anchors 12 and/or 14 with enough clearance such that the additional element(s) supports the movement of the moveable element 16 and help to align it relative to the anchors 12 and 14—this alignment provides precise and uniform motion in the elongate member 11.

In the embodiment illustrated in FIG. 1, an ultrasound transducer 24 is connected to the movable element of the actuator mechanism by being disposed on the moveable element.

In addition, while FIG. 1 shows only a single moveable element, multiple moveable elements are possible. For example, the SMA actuator 20 could be connected to a first moveable element, and the deformable component 22 could be connected to a second moveable element, with the transducer 24 disposed between the two moveable elements. Alternatively, the moveable element(s) can be eliminated and the SMA actuator 20 and the deformable component 22 can be attached directly to the ultrasound transducer 24.

In the embodiment shown in FIG. 1, the ultrasound transducer 24 is oriented such that it transmits ultrasound energy at an angle of about 90° relative to the longitudinal axes of the actuator mechanism 10 and elongate member 11. The angle of orientation of the ultrasound transducer 24 relative to the longitudinal axes can be any angle between about 15° and about 165°, with the preferred angle for side-looking ultrasound being between about 80° and about 110°. Angles contemplated include about 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, and about 165 degrees, or can fall within a range between any two of these values. For example, 15 (or 165, depending on orientation) degrees are preferred for forward-looking ultrasound imaging applications.

Housed in the elongate member 11, the actuator 10 shown in FIG. 1 can be used to generate movement of the moveable element 16 as shown in FIG. 2. By activating the SMA actuator 20, a force is generated which displaces the moveable element 16 and transducer 24 in a first direction since the anchor 12 is secured relative to the elongate member (not shown). FIG. 2a illustrates movement in a first direction, indicated by the arrow, which is rotational about the longitudinal axis of the actuator mechanism 10. FIG. 2c illustrates a movement in a first direction, indicated by the arrow, which is substantially parallel to the longitudinal axis of the actuator mechanism 10. The direction of movement generated by activation of the SMA actuator 20 will depend on configuration of the SMA actuator 20 relative to the anchor 12 and moveable element 16, as well as the shape which is trained into the SMA actuator 20. For example, the SMA actuator 20 shown in FIG. 2a is trained to twist when activated, while the SMA actuator 20' shown in FIG. 2c is trained to contract. A combination of rotational and longitudinal movements is possible as well, for example by using an SMA actuator trained to twist and extend or contract, or by using a combination of SMA elements or actuators. For example, two or more SMA actuators could be linked in series.

Figure 2A:
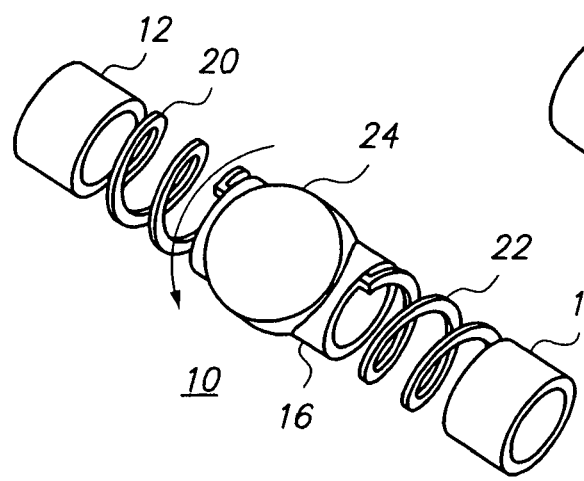
Figure 2B:
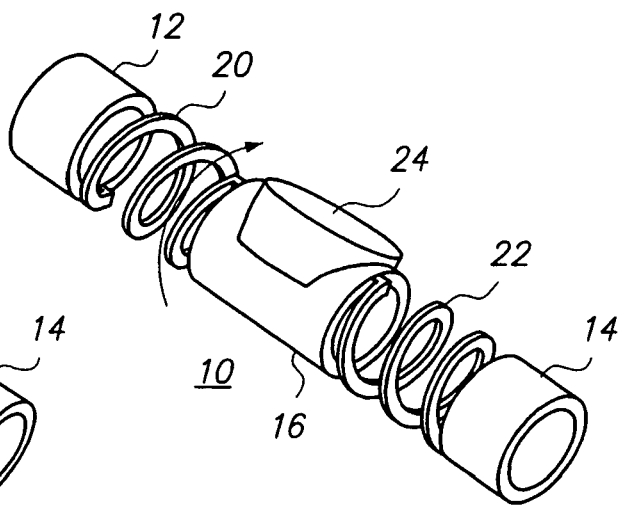
Figure 2C:
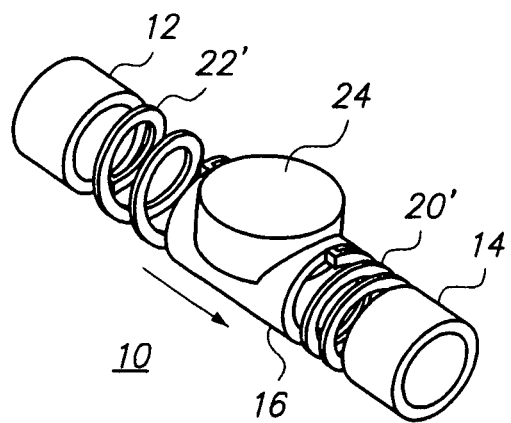
FIGS. 2c and 2d illustrate longitudinal motion of the actuator mechanism shown in FIG. 1.
Figure 2D:
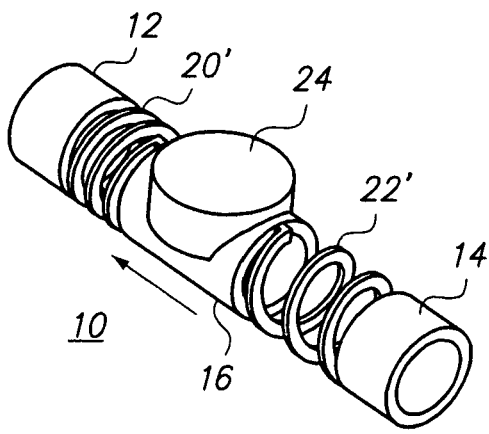

FIGS. 2b and 2d illustrate counter movements in a second direction, indicated by the arrows, which provides an oscillating movement to the moveable element 16 and transducer 24. This counter movement is provided by the deformable component 22 or 22', preferably when the SMA actuator 20 or 20' is deactivated. The deformable component 22 can be any elastic or superelastic material, or a second SMA actuator. The deformable component is in a relaxed state when the SMA actuator 20 or 20' is in the deactivated state. When the first SMA actuator 20 or 20' is activated, as shown in FIGS. 2a and 2c, the deformable component 22 or 22' is deformed by the movement of the moveable element 16 since the second anchor 14 is secured relative to the elongate member (not shown).

In an embodiment where the deformable component 22 or 22' is an elastic or superelastic material, the energy stored in the deformable component 22 or 22' when it is in its deformed state shown in FIGS. 2a and 2c moves the moveable element 16 and transducer 24 to the position shown in FIGS. 2b and 2d when the first SMA 20 or 20' is deactivated. This movement in the second direction, indicated by the arrow, is counter to the movement in the first direction. By alternately activating and deactivating the first SMA 20 or 20', a cyclical movement of the moveable element 16 and transducer 24 will result. This cyclical movement can be rotational about the longitudinal axis of the of the actuator mechanism 10 as shown in FIGS. 2a and 2b, or approximately parallel to the longitudinal axis of the actuator mechanism 10 as shown in FIGS. 2c and 2d, or a combination of rotational and longitudinal movement (not shown).

In a preferred embodiment, the deformable component 22 or 22' is a second SMA actuator that is trained to move the moveable element 16 and transducer 24 in a second direction which is counter the movement in the first direction caused by activation of the first SMA actuator 20 or 20'. In this embodiment, the cyclical motion is generated by the alternating activation of the first SMA actuator 20 or 20' and the second SMA actuator 22 or 22'. The activation of the first SMA actuator 20 or 20' deforms the second SMA actuator 22 or 22' which is in its inactive state, as illustrated in FIGS. 2a and 2c. The first SMA actuator 20 or 20' is deactivated and the second actuator SMA 22 or 22' is activated, causing the deformation of the first SMA actuator 20 or 20' and the movement of the moveable element 16 and transducer 24 as illustrated in FIGS. 2b and 2d.

Figure 3:
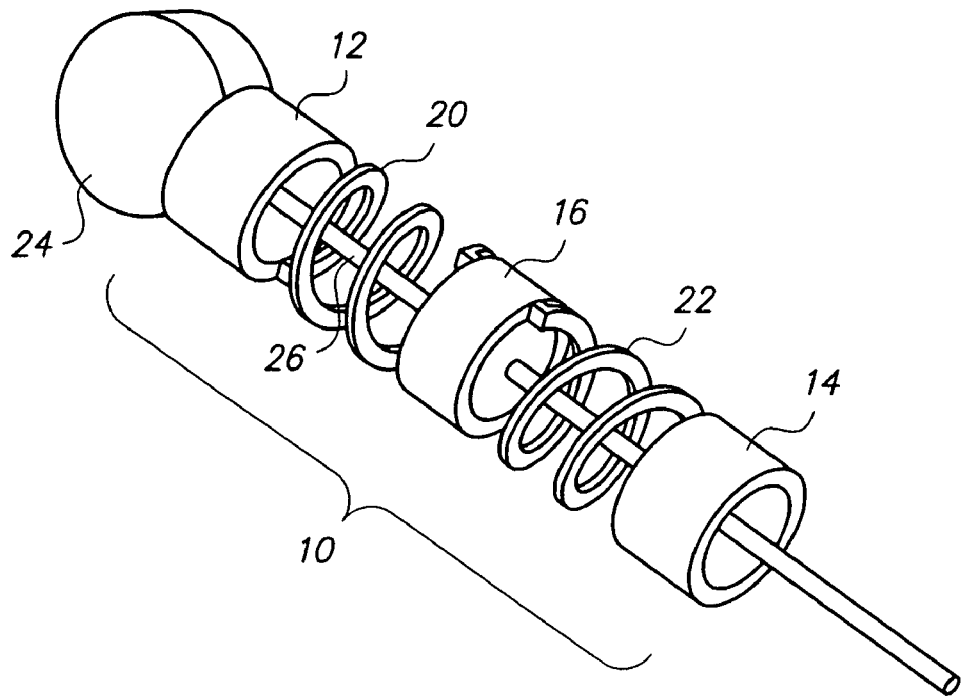
FIG. 3 is a perspective view showing an embodiment of the actuator mechanism of the present invention connected to an ultrasound transducer by a connecting arm.

FIG. 3 shows another embodiment of the invention including the actuator mechanism 10 illustrated in FIGS. 1 and 2. As in FIG. 1, the actuator mechanism 10 in FIG. 3 includes a first anchor 12, a second anchor 14, a movable element 16. The first anchor 12 is connected to the movable element 16 by a SMA actuator 20. The second anchor 14 is connected to the movable element 16 by a deformable component 22. In the embodiment illustrated in FIG. 3, the ultrasound transducer 24 is connected to the moveable element 16 by a connecting arm 26, such that movement of the moveable element 16 results in movement of the ultrasound transducer 24 and connecting arm 26. The movement of the moveable element 16 is generated as described above and illustrated in FIG. 2. In an alternate embodiment, the portion of the connecting arm 26 that is shown extending past the moveable element 16 and passing through the second anchor 14 is removed. The connecting arm 26 can have a lumen (not shown), and optionally wires can pass through the lumen to connect the transducer 24 to an ultrasound signal generator and processor located at the proximal end of the elongate member in which the actuator mechanism and transducer are housed. While the actuator mechanism 10 is illustrated as having the SMA actuator 20 in closer proximity to the transducer 24 than the deformable component 22, one of skill in the art will readily appreciate that the actuator mechanism 10 can be oriented such that the location of the SMA actuator 20 and the deformable component 22 are reversed.

In several embodiments disclosed herein, the connecting arm 26 is shown passing through the center of the anchor 12 and 14 and moveable element 16. One of skill in the art will recognize that it is not necessary to locate the connecting arm 26 along the longitudinal axis of the actuator mechanism 10. For example, the connecting arm 26 could be located on an exterior surface of the moveable element 16, and the anchor 12 could have a cut-out to allow the movement of the connecting arm 26 over the anchor 12. In addition, it can be desirable to provide structural supports for the moveable element 16 to stabilize its movement within the elongate member.

Figure 4:
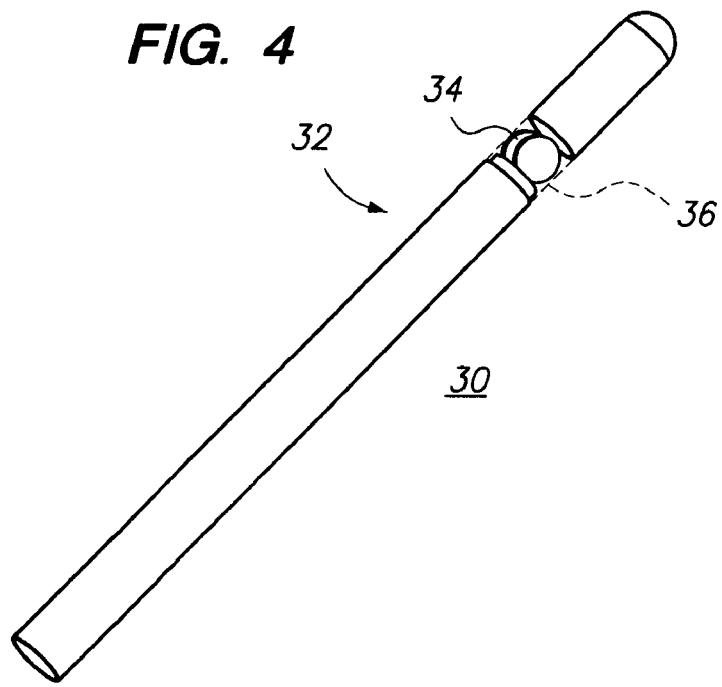
FIG. 4 is a perspective view of the device of FIG. 3 disposed in the distal end of an elongate member having an ultrasound transparent window.

FIG. 4 illustrates an elongate member 30 which has a distal end 32 in which the actuator mechanism and ultrasound transducer 34 are housed. The distal end 32 of the elongate member 30 has at least a portion 36 of the elongate member which is transparent to ultrasound energy. The ultrasound transducer 34 is oriented to transmit and receive ultrasound energy through this portion 36. The ultrasound transparent portion 36 can be a window made of an ultrasound transparent material, a material which is partially or substantially transparent to ultrasound energy, or the window can be a cut-out such that there is no material between the transducer and the outside environment. The portion 36 is desirable where the distal end 32 of the elongate member 30 is made of a substance that absorbs ultrasound energy. In an alternative embodiment, the entire distal end 32 or elongate member 30 is transparent to ultrasound energy.

Figure 5:
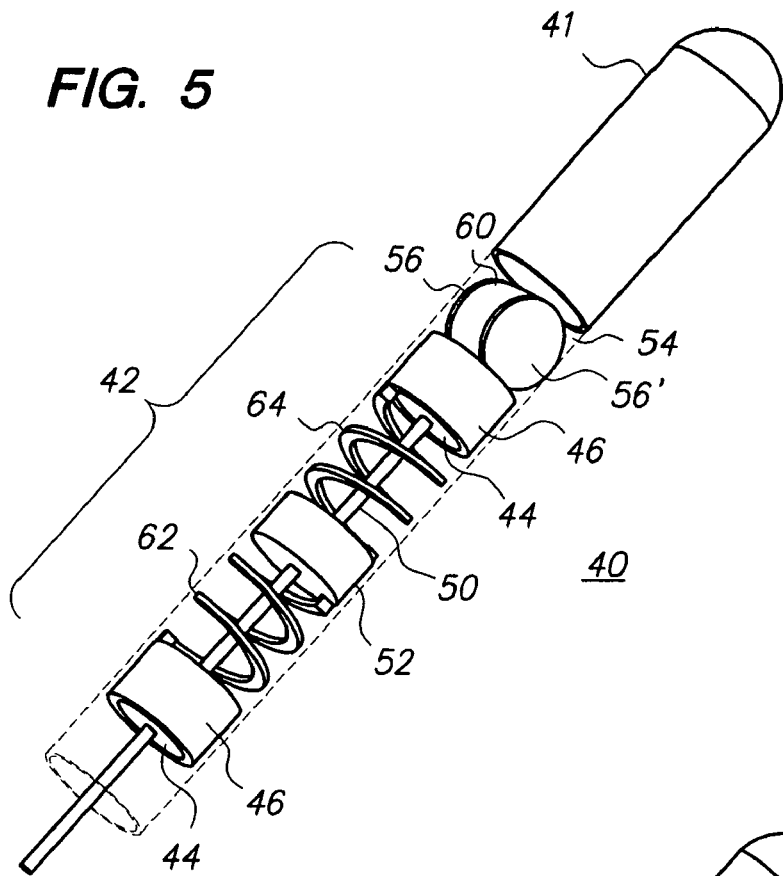
FIG. 5 is a perspective view of the distal end of an elongate member with an actuator mechanism and ultrasound transducer structure disposed therein.

FIG. 5 illustrates the distal end 40 of an elongate member, where all but the distal tip 41 of the elongate member is transparent so that the actuator mechanism 42 housed in the distal end 40 is visible. The actuator mechanism 42 is similar to the one illustrated in FIG. 3, with the addition of support members 44 disposed within the anchors 46. The support members 44 support the connecting arm 50, which connects the moveable element 52 and ultrasound transducer structure 54, acting to stabilize the movements of the connecting arm 50 and moveable element 52. The connecting arm 50 is free to rotate or slide within the support members 44, but not the moveable element 52. The support members 44 can be separate elements as shown in FIG. 5, or the anchors 46 can be fabricated to perform the function of the support members 44. The actuator mechanism 42 is used to generate movement of the moveable element 52, connecting arm 50 and ultrasound transducer structure 54 in the manner described above in reference to FIG. 2. The connecting arm 50 and moveable element 52 can be a single piece. In another embodiment, the moveable element 52 is eliminated, and the SMA actuator 62 and deformable component 64 are attached directly to the connecting arm 50.

In the embodiment shown in FIG. 5, the ultrasound transducer structure 54 has two ultrasound transducer crystals 56 and 56' for sending and receiving the ultrasound signal, which share a common backing 60. The backing 60 provides support for the transducer crystals 56 and 56', as well as a barrier to absorb the ultrasound energy emitted by the back face of the transducer crystals 56 and 56'. By using two transducer crystals 56 and 56', more of the interior wall of the vasculature or other structure can be imaged by a device of approximately the same size.

Figure 6:
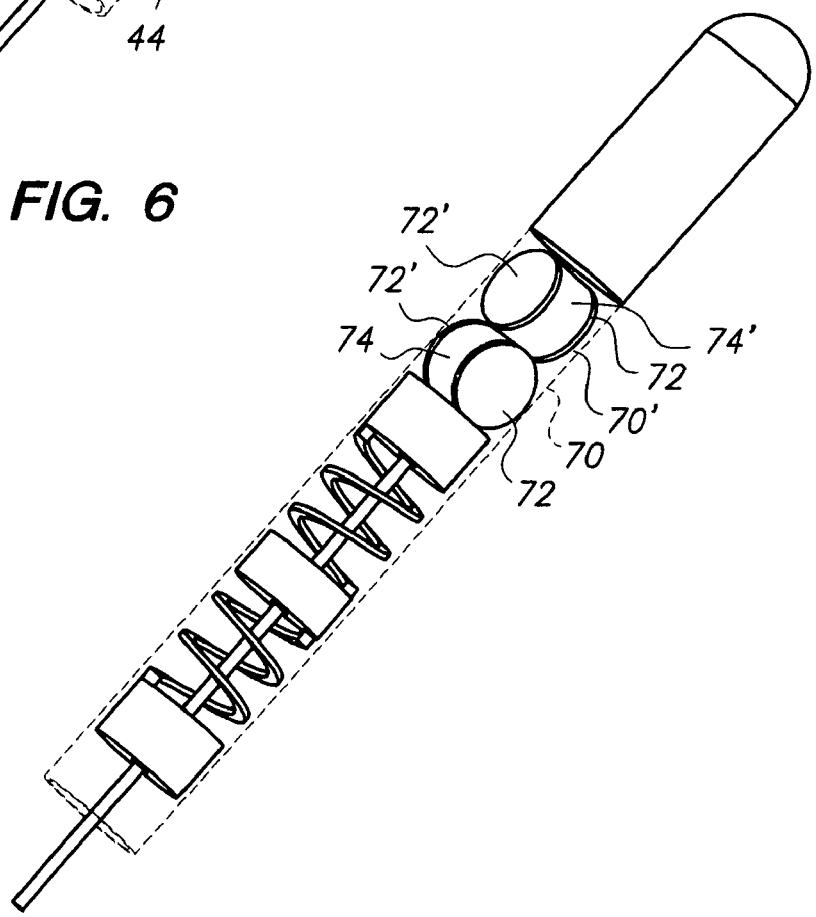
FIG. 6 is a perspective view of the distal end of an elongate member with an actuator mechanism and two ultrasound support structures stacked orthogonally.

FIG. 6 shows another embodiment wherein there are two ultrasound support structures 70 and 70' stacked orthogonally, with each transducer support structure 70 and 70' having two transducer crystals 72 and 72' sharing a common backing 74 and 74'. This configuration allows for an even larger field of view, as each transducer crystal 72 and 72' generates a signal oriented in a different direction. One of skill in the art will recognize that the ultrasound support structures 70 and 70' can be oriented to each other at any desirable angle. Additionally, the transducer crystals 72 and 72' can be oriented on the support structures 70 and 70' and with respect to each other in alternate configurations. Preferred embodiments of ultrasound transducers having more than one transducer crystal are described in more detail below and in reference to FIG. 12.

Figure 7:
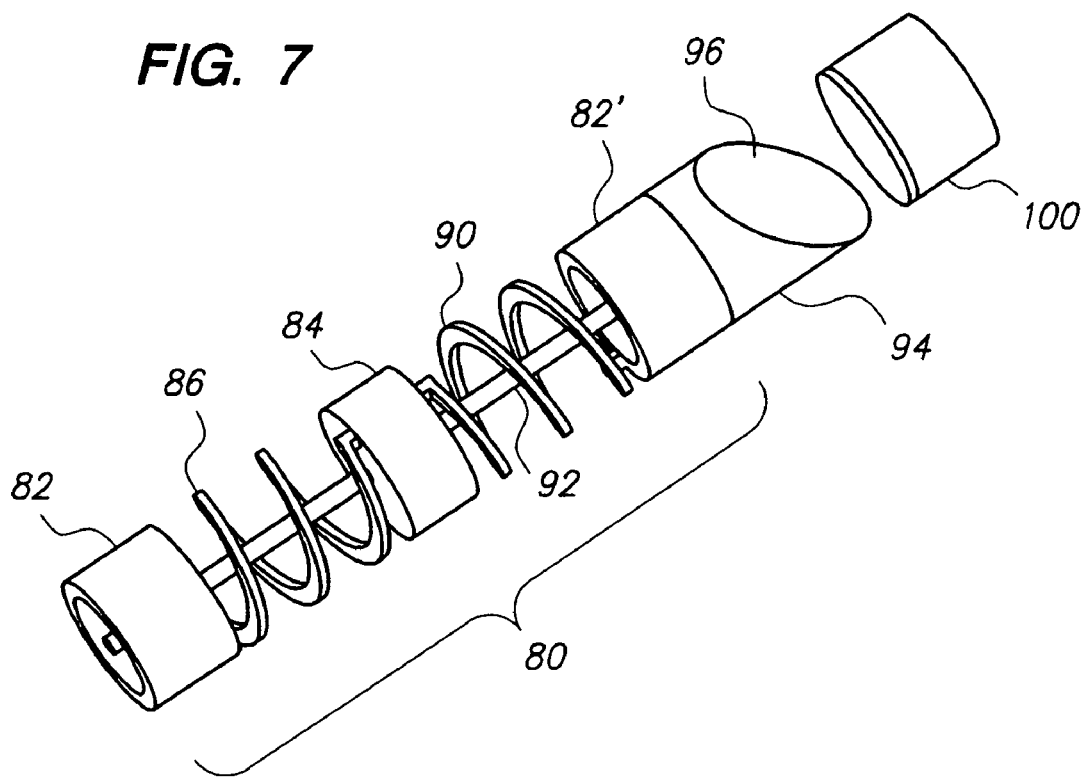
FIG. 7 is a perspective view showing an actuator mechanism with an ultrasound reflector connected by a connecting arm, with an ultrasound transducer aligned with the reflector.

FIG. 7 illustrates a preferred embodiment of the current invention. Shown in FIG. 7 is an actuator mechanism 80 which has two anchors 82 and 82', a moveable element 84 connected to the anchor 82 and 82' by an SMA actuator 86 and a deformable component 90. A connecting arm 92 connects the moveable element 84 to an ultrasound energy reflector 94. The reflector 94 has a surface 96 which is oriented to reflect ultrasound energy to and from an ultrasound transducer 100. Movement of the moveable element 84, connecting arm 92 and reflector 94 can be achieved as described above, with reference to FIG. 2. In another embodiment, the actuator mechanism 80 is configured to move the reflector 94 substantially parallel to the longitudinal axis of the actuator mechanism 80, as described above. One of skill in the art will recognize that to maximize longitudinal movement, a space can be introduced between the anchor 82' and the ultrasound energy reflector 94 to allow the reflector 94 to move in a proximal and distal direction. As discussed above, the orientation of the actuator mechanism 80 could be reversed such that SMA actuator 86 is closer to the reflector 94, and the deformable component 86 is more distant.

In the embodiment shown in FIG. 7, the transducer 100 and reflector 94 are oriented such that ultrasound energy is reflected from the transducer away from the device at an orthogonal angle, about 90°, relative to the longitudinal axes of the actuator mechanism 80 and elongate member (not shown). The angle of the reflector can be changed so that the ultrasound energy transmitted to and from the ultrasound transducer is at an angle between about between about 15° and about 165°, with the preferred angle for side-looking ultrasound being between about 80° and about 110°. Angles contemplated include about 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, and about 165 degrees, or can fall within a range between any two of these values. By decreasing the angle between the surface of the reflector and the surface of the transducer, the ultrasound energy will be reflected in a more forward-looking direction, that is toward the distal tip of the device. This can be useful in some applications where it is desirable to image the area in front of the device, such as when navigating a tortuous path through a blockage in the vasculature.

In the embodiment shown in FIG. 7, the reflector 94 can be shaped for specific purposes. For example, the surface 96 can be concave to focus the ultrasound beam into a smaller beam for certain imaging requirements. In other embodiments the surface is convex. In other embodiments, the reflector 94 has more than one reflective surface.

Figure 8:
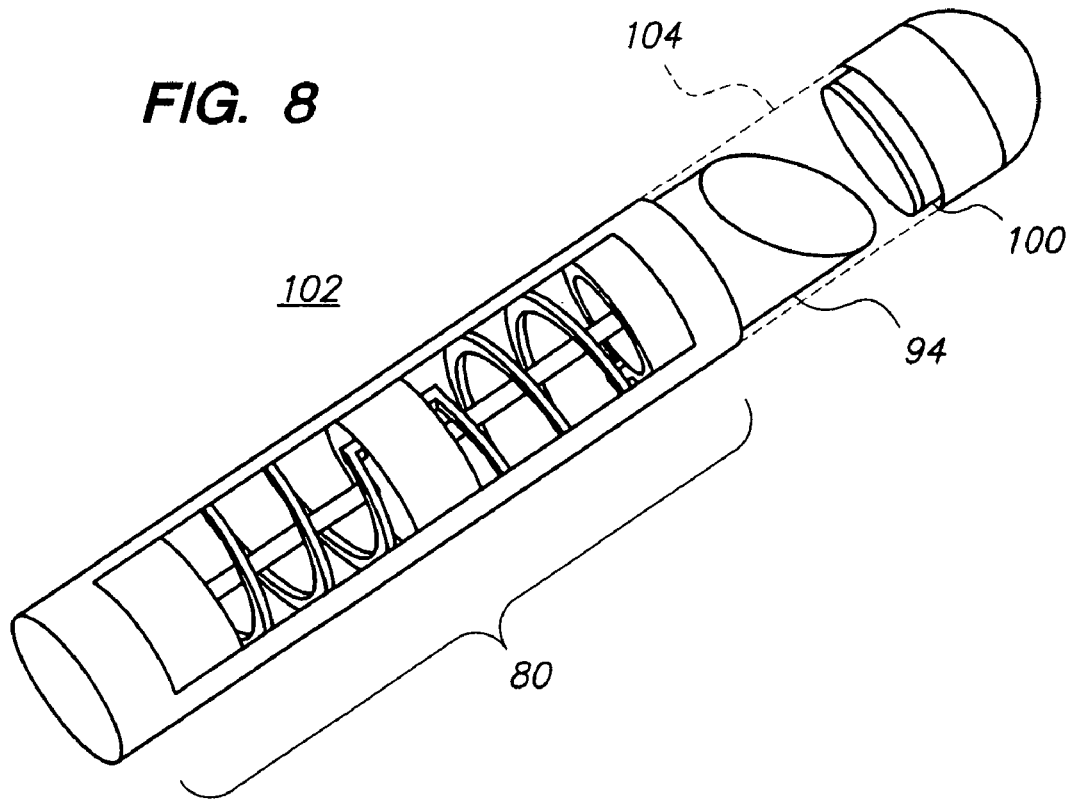
FIG. 8 is a partial cut-away perspective view showing the device of FIG. 7 housed in the distal end of an elongate member with an ultrasound transparent window.

FIG. 8 is a partial cut-away view which illustrates the device of FIG. 7 housed in the distal end 102 of an elongate member. A portion of the distal end housing the actuator mechanism 80 is cut away to show the actuator mechanism 80. The portion of the distal end adjacent to the reflector 94 is a window 104 which is transparent to ultrasound energy. This permits ultrasound energy to be transmitted to and from the ultrasound transducer 100 through the distal end 102 of the elongate member. Alternatively, the configuration of the actuator mechanism 80 and the transducer 100 can be reversed—the actuator mechanism 80 is housed in the distal end of the elongate member and the transducer is located closer to the proximal end of the device.

Figure 9:
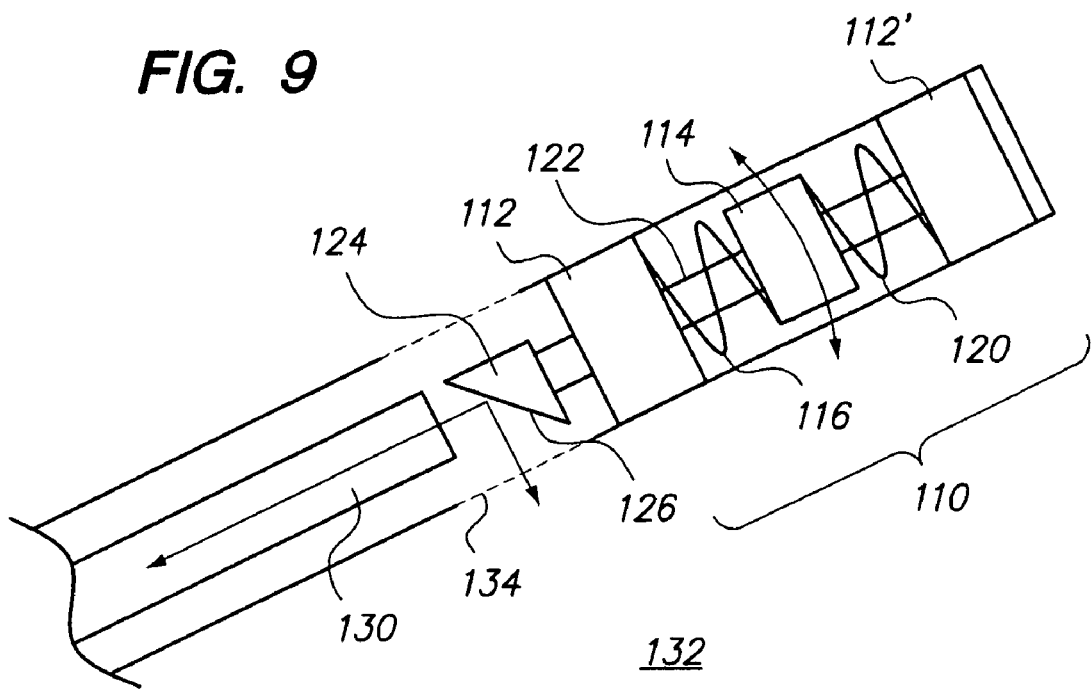
FIG. 9 is a schematic drawing of an optical coherence tomography device with an actuator mechanism, a reflector and an optical fiber disposed in an elongate member having a transparent window.

FIG. 9 is a schematic diagram of another embodiment of the current invention, where the imaging apparatus uses optical coherence tomography. OCT relies on light emitted from a fiber optic which is directed to the surface of the vasculature being imaged. The imaged surface reflects light back to the device where the same or another fiber optic transmits the signal to a processor outside the patient. Based on differential reflectance of the surface, and image is formed from the signal. FIG. 9 illustrates an actuator mechanism 110 similar to the ones disclosed in the previous figures, which has two anchors 112 and 112', a moveable element 114 connected to the anchors 112 and 112' by an SMA actuator 116 and a deformable component 120. A connecting arm 122 connects the moveable element 114 to a reflector 124. The reflector has a surface 126 which is oriented to reflect light energy to and from an optical fiber 130. The actuator mechanism 110, connecting arm 122 reflector 124 and fiber optic 130 are advantageously housed in the distal end of an elongate member 132. The apparatus further includes a window 134 that is transparent to light energy, located at the distal end of the elongate member 132.

While the connecting arm 122 is free to move relative to the anchors 112 and 112', it is secured to the moveable element 114. Movement of the moveable element 114, connecting arm 122 and reflector 124 can be achieved as described above with reference to FIG. 2. Rotational movement of the reflector 124 about the longitudinal axes of the actuator mechanism 110 and elongate member 132 is illustrated by the arrow in FIG. 9. In another embodiment, the actuator mechanism 110 is configured to move the reflector 124 substantially parallel to the longitudinal axes, as previously described. Also as discussed above, the connecting arm 122 can be supported by the anchors 112 and 112' or support elements disposed in the anchors. One of skill in the art will recognize that the connecting arm 122 and moveable element 114 can be fabricated from a single piece of material, or be separate pieces secured together, for example by glue, welding, snap-fit, or frictional forces due to a tight fit. These are examples only, and are not limiting. In an alternative embodiment, the SMA actuator 116 and deformable component 120 are attached directly to the connecting arm 122.

Since the optical fiber 130 is stationary and not mounted on the actuator mechanism 110, it eliminates the rotational load associated with conventional OCT devices which require rotating the entire length of the optical fiber. As a result, the actuator mechanism can potentially generate a wider range of motion due to the smaller load associated with the connecting arm 122 and reflector 124. Since the OCT imaging device is based on a sweeping reflector, the fiber optic is can remain motionless, reducing or eliminating image distortion and issues associated with the torque generated by the spinning optical fiber.

The reflector 124 can be shaped for specific purposes. For example, the surface 126 can be concave to focus the coherent light into a smaller beam for certain imaging requirements. In other embodiments the surface is convex. The surface 126 can be designed to replace the lens typically attached to the end of a fiber optic when used for OCT. In this case the reflector 124 is used to focus the coherent light at the distance needed to image the vasculature, and the lens is not necessary. In some embodiments the reflector 124 is a mirror, in others, it is a prism. A prism allows refractive optical coherence tomography (as opposed to reflective tomography using a mirror.) The prism can also be designed to replace the lens typically required at the distal tip of the optical fiber. In other embodiments, the reflector 124 has more than one reflective surface. In another embodiment, one or more additional optical fibers and/or reflectors are provided to increase the field of view, or to provide different wavelengths of light.

Figure 10:
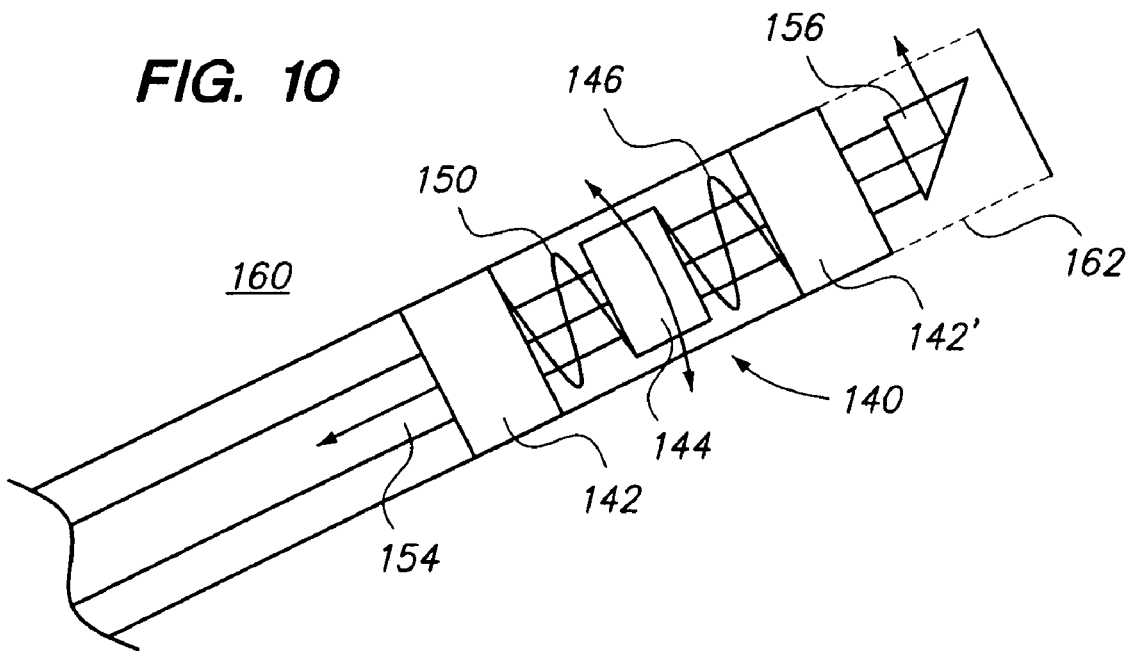
FIG. 10 is a schematic drawing of another embodiment of an optical coherence tomography device with an actuator mechanism connected to an optical fiber with a reflector on its distal end, disposed in an elongate member having an transparent window.

FIG. 10 is a schematic of another embodiment of the invention where the actuator mechanism 140 rotates the distal end of the fiber optic used for OCT. FIG. 10 illustrates an actuator mechanism 140 which has two anchors 142 and 142', a moveable element 144 connected to the anchors 142 and 142' by an SMA actuator 146 and a deformable component 150. The moveable element 144 is secured to the distal end of a fiber optic 154 by, for example but not limited to, crimping, glue, welding, snap-fit, set screw, or frictional forces due to a tight fit. The optical fiber 154 which has a prism 156 or other reflective surface mounted on its distal tip. The prism 156 has a surface oriented to refract light energy to and from the optical fiber 154 as illustrated by the arrows. The actuator mechanism 140, fiber optic 154 and prism 156 are shown housed in the distal end of an elongate member 160. In the embodiment shown in FIG. 10, a portion of the distal end of the elongate member is a window 162 that is transparent to light energy.

While the optical fiber 154 is free to move relative to the anchors 142 and 142', it is secured to the moveable element 144. Movement of the moveable element 144 can be achieved as described above, and as illustrated in FIG. 2. Because the moveable element 144 is secured to the fiber optic 154, rotational movement of the moveable element as illustrated by the arrow in FIG. 10 results in rotational movement of the distal end of the fiber optic 154 and prism 156 about the longitudinal axis of the elongate member.

The sweeping motion of the actuator mechanism 140 creates a scanning pattern and can achieve a field of views in a range of angles, depending upon the strain characteristics of the optical fiber 154. This produces the required scanning motion for OCT imaging without requiring the rotation of the entire fiber optic and the high-speed mechanical rotator in the proximal end of the device. In another embodiment, one or more additional actuator mechanisms are spaced along the fiber optic from the distal end toward the proximal end, increasing the rotational displacement of the distal end or the entire length of the optical fiber, and distributing the rotational load generated along the length of the optical fiber.

Figure 11:
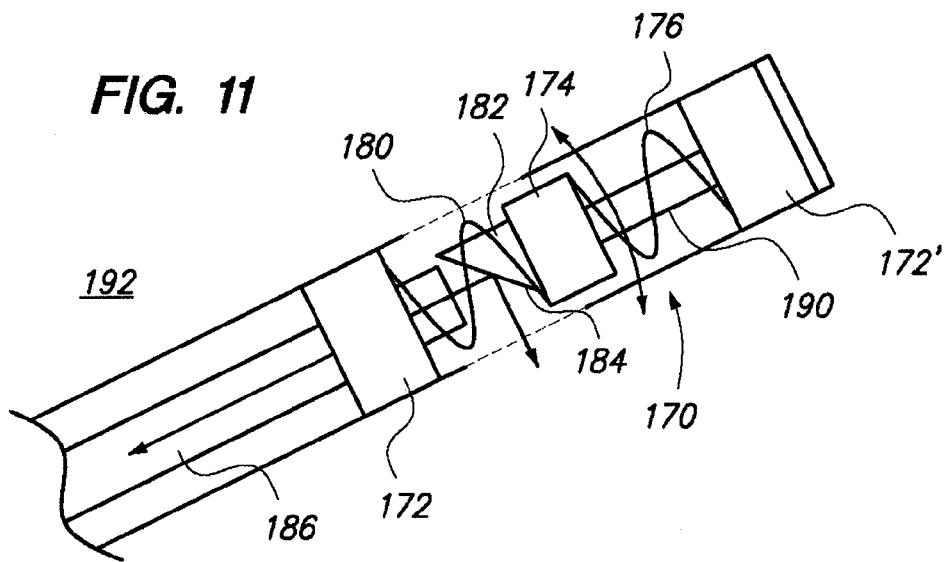
FIG. 11 is a schematic drawing of another embodiment of an optical coherence tomography device with an actuator mechanism, a reflector and an optical fiber disposed in an elongate member having a transparent window.

FIG. 11 is a schematic illustration of an actuator mechanism 170, which has two anchors 172 and 172', a moveable element 174 connected to the anchors 172 and 172' by an SMA actuator 176 and a deformable component 180. A reflector 182 is mounted on the moveable element 174. The reflector has a surface 184 which is oriented to reflect light energy to and from an optical fiber 186. An optional support structure 190 stabilizes the moveable element 174. The actuator mechanism 170, reflector 182 and fiber optic 186 are shown housed in the distal end of an elongate member 192 as shown in FIG. 9. The actuator mechanism provides cyclical movement of the moveable element 174 and reflector 182 as described previously.

FIGS. 9, 10 and 11 illustrate a reflector or prism oriented such that light energy is reflected from the fiber optic away from the device at an orthogonal angle, about 90°, relative to the longitudinal axes of the actuator mechanism and elongate member. The angle of the reflector can be changed so that the light energy transmitted to and from the fiber optic is at an angle between about 15° and about 165° relative to the longitudinal axis of the device, with the preferred angle being between about 80° and about 110°. Angles contemplated include about 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, and about 165 degrees or can fall within a range between any two of these values. By adjusting the angle between the reflective surface of the reflector or prism and the end of the fiber optic, the light can be reflected in a more forward-looking direction, that is toward the distal tip of the device. This can be useful in some applications where it is desirable to image the area in front of the device, such as when navigating a tortuous path through a blockage in the vasculature.

As described herein, at least a portion of the elongate member is transparent to ultrasound energy or light energy. This includes a window made of an ultrasound or light energy transparent material, a material which is partially or substantially transparent to ultrasound or light energy, or the window can be a cut-out such that there is no material between the transducer, reflector or prism and the outside environment. In other embodiments the entire distal end or elongate member is transparent.

The actuator described herein can be made very small, such that the actuator has a diameter/width between about 5 μm and about 1000 μm, with the preferred size being between about 5 μm and about 100 μm. The actuator preferably has a diameter or width of, or of about, 5, 10, 20, 30, 40, 50, 60, 70, 80, 90, 100, 200, 300, 400, 500, 600, 700, 800, 900, or 1000 μm, or is at least about, 5, 10, 20, 30, 40, 50, 60, 70, 80, 90, 100, 200, 300, 400, 500, 600, 700, 800, 900, or 1000 μm, or is no more than about 5, 10, 20, 30, 40, 50, 60, 70, 80, 90, 100, 200, 300, 400, 500, 600, 700, 800, 900, or 1000 μm, or can fall within a range between any two of these values. The range of lengths preferred for the actuator is quite broad, and depends on the application. For rotational motion, the length of the actuator mechanism can be from about 20 μm to about 10 mm, with the preferred size being from about 200 μm to about 10 mm. For longitudinal motion, the length of the actuator can be from about 100 μm to about 20 mm, with the preferred length being from about 1 mm to about 20 mm. The actuator preferably has a length of, or of about, 20, 30, 40, 50, 60, 70, 80, 90, 100, 200, 300, 400, 500, 600, 700, 800, 900 μm, 1, 2, 3, 4, 5, 6, 7, 8, 9, 10, 11, 12, 13, 14, 15, 16, 17, 18, 19, or 20 mm, or is at least about, 20, 30, 40, 50, 60, 70, 80, 90, 100, 200, 300, 400, 500, 600, 700, 800, 900 μm, 1, 2, 3, 4, 5, 6, 7, 8, 9, 10, 11, 12, 13, 14, 15, 16, 17, 18, 19, or 20 mm, or is no more than about 20, 30, 40, 50, 60, 70, 80, 90, 100, 200, 300, 400, 500, 600, 700, 800, 900 μm, 1, 2, 3, 4, 5, 6, 7, 8, 9, 10, 11, 12, 13, 14, 15, 16, 17, 18, 19, or 20 mm, or can fall within a range between any two of these values.

The outside diameter of the elongate member, such as a guide wire or catheter containing an imaging device described herein can be as small as from about 0.005" to about 0.100" outside diameter. Preferably, the outside diameter of the elongate member is, or is about 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 hundredths of an inch, or is at least about, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 hundredths of an inch, or is no more than about 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 hundredths of an inch, or can fall within a range between any two of these values.

The range of motion generated by the actuator mechanism described herein will vary depending of the application. Rotational motion can be in a range from about 1 or 2 degrees up to about 400 degrees, depending on the area of interest. Angles of rotational displacement generated by the actuator mechanism are, or are about, 1, 2, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395 or 400 degrees, or at least about 1, 2, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, or 400 degrees, or no more than 1, 2, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, or 400 degrees, or can fall within a range between any two of these values. By adjusting the power and/or duration of the activation signal to one or more of the SMA actuators, the degree of rotation or length of longitudinal displacement can be adjusted while the device is in the patient, allowing the operator to adjustably define a specific image field of view. The preferred range of rotational displacement generated by the actuator device is from about 25 to 360 degrees. In addition, it is possible to use the device of the invention for singe point interrogation for optical coherence reflectometry or Doppler effect measurements.

The amount of longitudinal displacement generated by the actuator mechanism is also dependent on the length of the area of interest. The length of longitudinal displacement can be from about 100 μm to about 30 mm or more. The length of longitudinal displacement generated by the actuator mechanism preferably is, or is about 100, 200, 300, 400, 500, 600, 700, 800, 900 μm, 1, 2, 3, 4, 5, 6, 7, 8, 9, 10, 11, 12, 13, 14, 15, 16, 17, 18, 19, 20, 25, or 30 mm, or is at least about, 100, 200, 300, 400, 500, 600, 700, 800, 900 μm, 1, 2, 3, 4, 5, 6, 7, 8, 9, 10, 11, 12, 13, 14, 15, 16, 17, 18, 19, 20, 25, or 30 mm, or is no more than about 100, 200, 300, 400, 500, 600, 700, 800, 900 μm, 1, 2, 3, 4, 5, 6, 7, 8, 9, 10, 11, 12, 13, 14, 15, 16, 17, 18, 19, 20, 25, or 30 mm, or can fall within a range between any two of these values.

The frequency of the motion generated by the actuator mechanism can range from about 1 Hz to about 100 Hz. The preferred frequency of motion is between about 8 Hz and 30 Hz. The frequency of movement generated by the actuator mechanism is, or is about, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 Hz, or at least about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 Hz, or no more than about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 Hz, or can fall within a range between any two of these values.

In some embodiments, the actuator mechanism disclosed herein is made without any mechanical joints.

When the actuator described above is used to generate movement of an ultrasound transducer, the area imaged by a single transducer is limited by the range of movement the actuator can generate. One way to achieve a larger field of view is to use multiple transducer crystals. The prior art discloses phased array devices where individual crystal transducers are used in combination to generate an ultrasound wave for imaging. In these prior art devices, the individual crystals are mounted on separate backings and are not capable of individually producing an ultrasound signal for imaging. In contrast, the individual transducer crystals used in the transducers of the instant are preferably mounted on a shared backing and are preferably capable of individually producing an ultrasound signal for imaging.

As used herein, transducer crystal or crystal transducer refers to the material used to produce and/or receive the ultrasound signal. Materials used for making the transducer crystal are known in the art and include quartz and ceramics such as barium titanate or lead zirconate titanate. Ultrasound transducer crystals for IVUS utilize frequencies from about 5 MHz to about 60 MHz, with the preferred range being from about 20 MHz to about 45 MHz.

Ultrasound crystals are preferably substantially rectangular, square, elliptical, or circular, although any shape that produces a functional ultrasound transducer is contemplated. As used herein, the top and bottom edge of a transducer crystal are defined by substantially parallel lines bounding the transducer, a first and second side edge are defined by a second set of substantially parallel lines bounding the transducer, where the lines defining the top and bottom edges are substantially perpendicular to the lines defining the first and second side edges. As defined herein, ellipses, circles, irregular shapes, etc. can have top, bottom, first and second edges.

FIG. 12 illustrates a schematic of ultrasound transducers having one, two or three crystal transducers. The dashed lines shown in FIG. 12 represent the direction the ultrasound energy is transmitted and received from the transducer crystals. FIG. 12a shows an ultrasound transducer 200 having one crystal transducer 202 on a backing structure 204. The backing material can be any material known to those in the art which absorbs ultrasound energy radiated from the transducer crystals back face. FIG. 12b shows an ultrasound transducer 210 having two crystal transducers 212 and 214 on a single backing structure 216. FIG. 12c shows an ultrasound transducer 220 having three crystal transducers 222, 224 and 226 on a single backing structure 228.

Figure 12A:
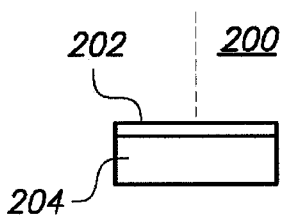
FIGS. 12a, 12b, and 12c are schematic drawings illustrating ultrasound transducers having one, two, or three individual transducer crystals, respectively.
Figure 12B:
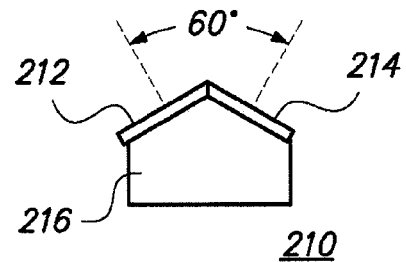
Figure 12C:
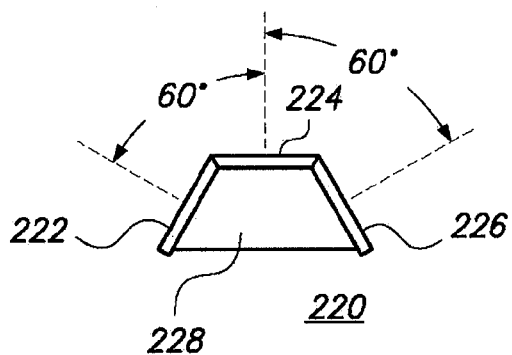
Figure 12D:
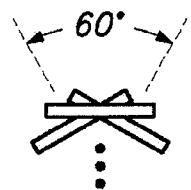
FIGS. 12d, 12e, and 12f illustrate the field of view obtained by rotating the transducers of FIGS. 12a, 12b, and 12c, respectively.
Figure 12E:
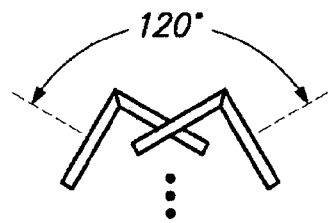
Figure 12F:
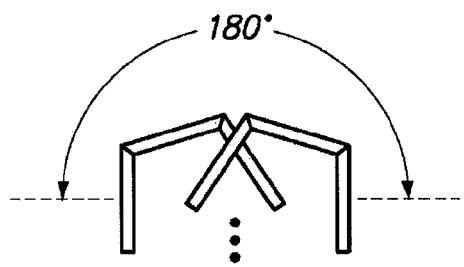

FIGS. 12d, 12e, and 12f show the range of fields of view with the different configurations of transducers shown in FIG. 12a, 12b and 12c, respectively. As an example, assume that the actuator mechanism (not shown) used to move the transducer can generate 60° rotational motion. With a single transducer as shown in FIG. 12a, rotation of the ultrasound transducer 200 through 60° will provide a 60° field of view as shown in FIG. 12d, where the crystal transducer 202 is shown at the two extremes of the range of motion (the backing 204 is excluded for clarity.) If two transducers 212 and 214 are arranged with a 60° angle between their respective fields of view as shown in FIG. 12b, rotating the transducer structure 210 through 60° as shown by the two positions illustrated in FIG. 12e will provide a field of view totaling 120° with the same actuator. Similarly, three-transducers configured with a 60° angle between each crystal transducer 222, 224 and 226 as shown in FIG. 12c will have a field of view equivalent to 180° if the transducer is rotated through 60° as shown in FIG. 12f.

Although a 60° angle between the beams of the transducer crystals is shown in FIG. 12, any angle between 0° (equivalent to the field of view provided by a large crystal) and 180° is encompassed by the present invention. Angles encompassed by the invention include about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, and about 180 degrees, or can fall within a range between any two of these values. In some embodiments, the angles defined by the adjacent pairs of crystals are not equal. For example, where three crystals are used, the angle defined by the third crystal and the second crystal can be different than the angle defined by the first crystal and the second crystal. The angle between the faces of the transducer crystals is preferably about the same as the degrees of deflection which can be achieved by the actuator mechanism. This maximizes field of view without significant overlap or gaps between the individual fields of view for each transducer crystal. For example, if two crystal transducers 212 and 214 are aligned at 60° as illustrated in FIG. 12b, but the actuator can only rotate the transducer structure by 30°, there will be a gap of approximately 30° between the fields of view generated by each transducer crystal. Similarly, if the actuator can rotate through 90°, there will be a 30° field of view overlap between the two fields of view generated by each transducer crystal. While an overlap or gap in the fields of view can be desirable in some applications, the preferred embodiment provides for minimal gaps or overlaps. Importantly, the individual transducer crystals are placed with their edges adjacent or touching, such that the size of any gap between the fields of view of the individual crystal transducers is minimized and significantly reduced. In a preferred embodiment, the individual transducer crystals are configured such that any gap between the individual fields of view are substantially eliminated. This provides an improved image quality.

While FIG. 12 illustrates an ultrasound transducer with 1, 2, or 3 crystals, more crystals can be used. Also contemplated are ultrasound transducers with 4, 5, 6, 7, 8, 9, or 10 transducer crystals. The crystals can be arranged on a single backing device, or on multiple backing devices as illustrated in FIG. 6. For single crystal transducers the diameter of the crystal if circular shaped, or width if rectangular shaped, is preferably from about 10 μm to about 10 mm, and more preferably from about 100 μm to about 1 mm. For transducers with multiple crystals, the combined diameter or width of the individual crystals is preferably from about 10 μm to about 10 mm, and more preferably from about 100 μm to about 1 mm. Preferably, the diameter or width of the individual crystals on a given transducer is approximately equal, although crystals of different diameters or widths can be combined. The individual transducer crystals preferably have a diameter or width of, or of about, 100, 200, 300, 400, 500, 600, 700, 800, 900, or 1000 μm, or are at least about, 100, 200, 300, 400, 500, 600, 700, 800, 900, or 1000 μm, or are no more than about 100, 200, 300, 400, 500, 600, 700, 800, 900, or 1000 μm, or can fall within a range between any two of these values.

In another embodiment, the multiple transducer configurations disclosed herein are utilized in a device in which the actuator is configured to provide longitudinal, rather than rotational motion, for example as shown in FIGS. 2c and 2d. As with the rotational movement illustrated in FIG. 12, combining multiple transducers with longitudinal motion can also provide a larger field of view with the same actuator.

The multiple transducer configuration disclosed herein can also be used for forward looking ultrasound devices. Providing a 180° field of view allows ultrasound imaging with the capability of side-looking as well as forward-looking in a single device. A preferred forward looking device is disclosed in U.S. Patent Publication No. US-2004-0056751-A1, which is herein incorporated by reference in its entirety. Other forward looking devices include those disclosed in U.S. Pat. Nos. 5,379,772 and 5,377,685, which are herein incorporated by reference. As used herein, a pivot point is a point around which the transducer is rotated, and includes mechanical joints, for example those disclosed in U.S. Pat. No. 5,379,772, FIGS. 2, 5, and 6. While the aforementioned forward looking devices disclose a single crystal transducer, applicants have discovered that transducers having multiple crystals dramatically increase the field of view. As was described with reference to side-looking devices, the multiple crystal transducers are disposed on the actuator mechanism.

U.S. Patent Publication No. US-2004-0056751-A1 discloses an elastic or superelastic material utilized as a structural material for a micromanipulator. In principle, when a compliant mechanism is deformed with an actuator, strain energy is stored inside the underlying structure during deformation (elastic and plastic). The stored energy is then directly utilized to produce a bias force to return the structure to its original shape. However, an elastic material such as stainless steel can also be utilized as a structural material for compliant mechanisms According to an aspect of the disclosure, a Nd:YAG laser is implemented in the fabrication of the compliant structure out of a tube. A tubular nitinol structure with compliant mechanism was successfully fabricated using laser machining with a laser beam size of about 30 μm. The outer diameter of the tube is about 800 μm and the wall thickness is about 75 μm. Actual feature size is about 25 μm, which is mostly limited by the size of the laser beam. Thus, by reducing the beam size, resolution of the laser machining can be enhanced.

To shape a nitinol structure, there are three fabrication processes currently commercially available: chemical etching, laser machining and micro-mechanical cutting. However, these two processes are not able to precisely control etching depth. Thus, it is very difficult to have a variation in thickness and, consequently, the thickness of the mechanism determines the substrate thickness. This presents another issue in design, which is structural rigidity. For instance, if the substrate thickness is on the order of tens of microns, the supporting structure also starts deflecting as the mechanism moves. This deflection at the supporting structure, which is supposed to be fixed, directly contributes to loss of output displacement. Structural rigidity is mostly a shape factor, which is related to flexural modulus, EI. Considering the structural rigidity, a tube shape is more attractive than a plate form.

Figure 13A:
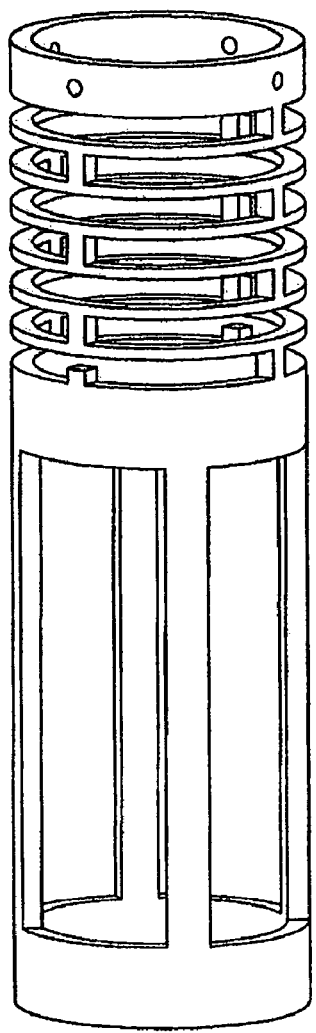
FIGS. 13a and 13b are perspective views showing two tubular structures each with a built-in compliant mechanism in different design configuration.
Figure 13B:
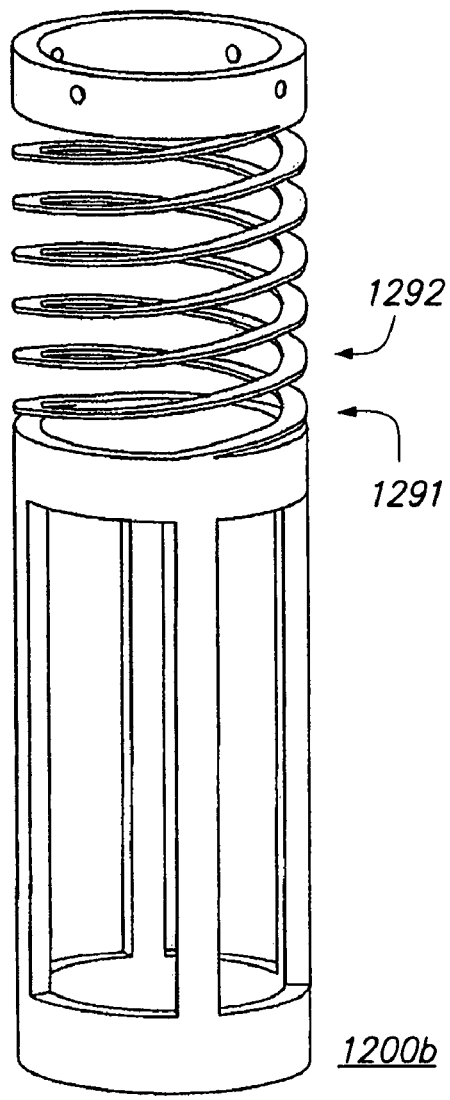

FIG. 13a illustrates an exemplary tubular structure 1200a with a built-in compliant mechanism 1201a. FIG. 13b illustrates another exemplary tubular structure 1200b with a built-in compliant mechanism 1201b in a helical configuration having helix 1291 and helix 1292 intertwined in a "double helix"-like fashion. The mechanism design can be any shape and/or configuration as long as it utilizes structural compliance (elasticity and/or superelasticity) as a main design parameter. Similarly, as one skilled in the art would appreciate, the rest of the tubular structure can be in any suitable configuration, size and length, etc., optimized for a particular application and thus is not limited to what is shown here.

Moreover, in addition to nitinol, other flexible, resilient biocompatible metal or polymer materials can also be utilized as long as they have reversible structural behaviors, i.e., have elastic and/or superelastic behaviors while actuated.

As illustrated in FIG. 13b, compliant mechanisms can be in a "double helix" configuration. U.S. Patent Publication No. US-2004-0056751-A1 teaches that it is desirable with the disclosed invention that any bending strain of the compliant mechanisms is distributed substantially evenly along their entire lengths. This reduces peak strain, which in various embodiments, can be, 4% or less, 3% or less, 2% or less and 1% or less. The "double helix" configuration provides greater symmetry in motion and provides a more even bending It is desired that the stiffness of compliant mechanisms in different directions be substantially the same.

In various embodiments, the elastic bending strength of the compliant mechanisms is customized in order to match with that of the actuators. In some embodiments, the actuators have slightly stiffer elastic bending strengths than those of the compliant mechanisms. In one embodiment, the compliant mechanisms are stiffer than the actuators when the actuators are relaxed, and the compliant mechanisms are softer than the actuators when the actuators are active. It is desirable to provide compliant mechanisms in configurations, such as those of the "double helix" configurations, that have as little stress concentration as possible.

According to the invention disclosed in U.S. Patent Publication No. US-2004-0056751-A1, the strain of a compliant mechanism is distributed, while minimizing the occurrence of strain location. The mechanical characterization of a compliant mechanism can be tuned by modifications in, (i) stiffness, (ii) peak strain (maximum strain), (iii) size, (iv) fatigue life, and the like. In one embodiment, the upper limit of strain is no more than 4%. The bending stiffness depends on actual application. By way of illustration, and without limitation, the bending stiffness of a compliant mechanism can be at least 0.5 N-mm and no more than 10 N-mm. In various embodiments, compliant mechanisms are stiffer than the imaging device. The associated actuators are also stiffer than the imaging device. The actuators need a longer thermal time constant than the imagining device.

Figure 14:
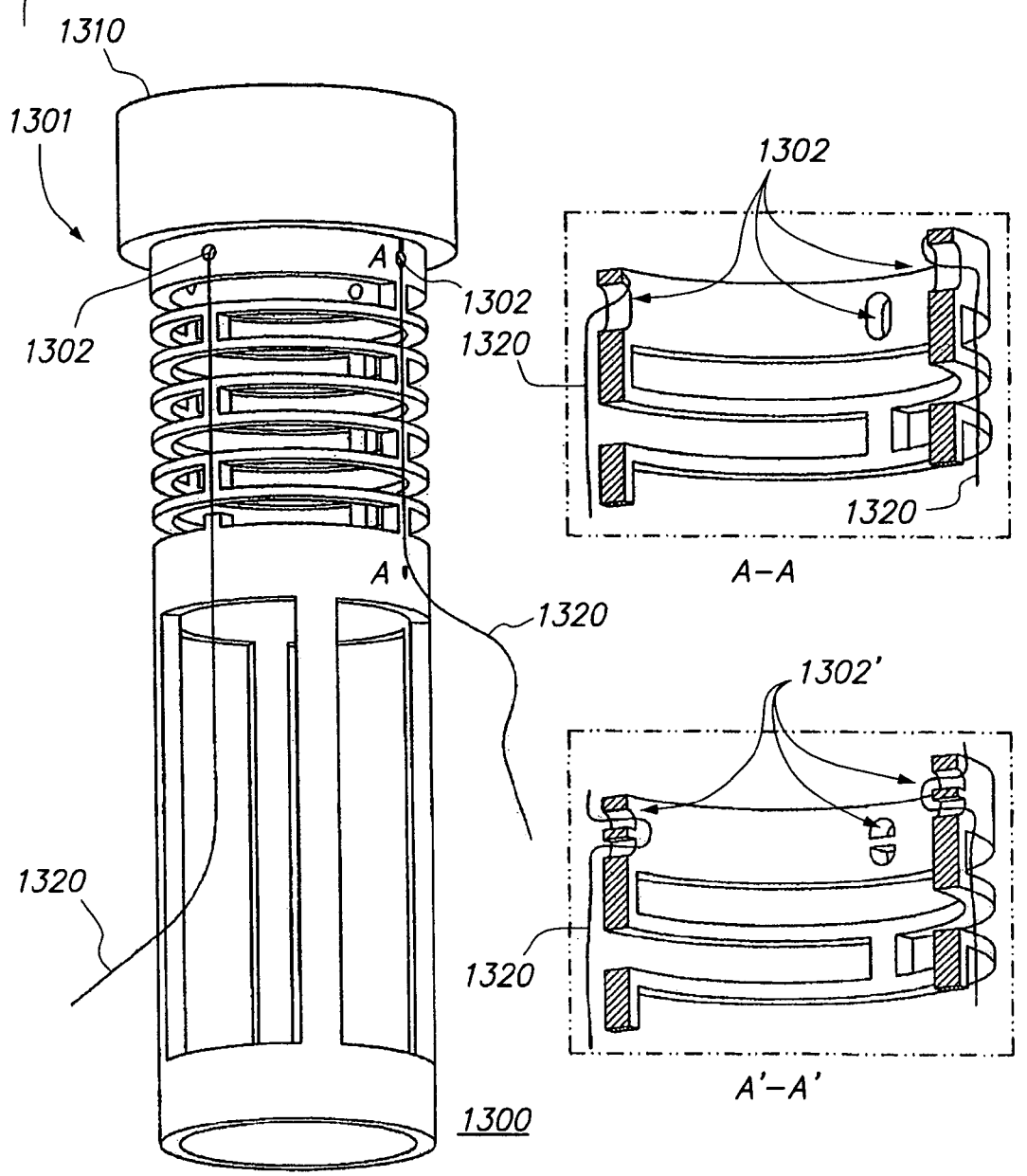
FIG. 14 is a perspective view showing an ultrasound transducer coupled to a micromanipulator having the compliant structure of FIG. 13a and two SMA actuators configured to actuate the compliant mechanism thereof.

FIG. 14 schematically shows, according to an aspect of the invention disclosed in U.S. Patent Publication No. US-2004-0056751-A1, a micromanipulator 1300 tightly coupled with an ultrasound transducer 1310 for image scanning. Micromanipulator 1300, as well as the other embodiments of micromanipulators disclosed herein, provide for steering, viewing and treatment at sites within vessels of the body, as well as for industrial applications.

The micromanipulator 1300 enables the ultrasound transducer 1310 to be directly coupled to the compliant mechanisms 1301. In this fashion, the rotational center of the transducer 1310 for the scanning motion is substantially closer to the rotational axis of the mechanism 1301. In an embodiment, SMAs are implemented as main actuators 1320 for the micromanipulator 1300. To allow the SMAs 1320 be attached thereto, the micromanipulator 1300 might have one or more attachment points or built-in micro structures such as welding-enabling structures 1302 as shown in a cross-sectional view A-A and clamping-enabling structures 1302' as shown in another cross-sectional view A'-A'. In some embodiments, the SMAs 1320 are attached to the compliant apparatus via the one or more attachment points or welding-enabling structure 1302 using a laser having a laser beam size of about 200 μm or less. In some embodiments, the SMAs 1320 are fastened to the compliant apparatus via the built-in clamping-enabling structures 1302'.

The compliant mechanisms 1301 are actuated with SMA 1320 actuators based on shape memory effects including contraction as well as rotation motion to maximize output displacement. As one skilled in the art can appreciate, the SMA actuators can be in any shape such as wire, spring, coil, etc. and thus is not limited to what is shown.

Another aspect of the current invention is a method for visualizing the interior of a patient's vasculature, or other structure with a lumen. The method comprises inserting the inserting the distal end of the elongate member of any of the apparatuses disclosed herein into the vasculature of a patient. The distal end is advanced through the vasculature, optionally under the guidance of x-ray fluoroscopic imaging to the location of the blockage, legion, or other area to be imaged. Alternatively, the imaging device can be used instead of or in addition to the x-ray fluoroscopic imaging to guide the device through the vasculature.

To generate an image, an ultrasound signal generator/processor located outside the patient is activated, generating an ultrasound signal from the ultrasound transducer. The actuator mechanism described herein is used to generate a cyclical movement of the ultrasound transducer or reflector as described above. In the case of OCT, the fiber optic is used to transmit a light signal from a signal processor unit outside the patient to the distal tip of the optical fiber. The reflector, prism, or distal end of the optical fiber is moved in a cyclical motion by the actuator mechanism as described herein. The cyclical movement sweeps the ultrasound or light energy over the area being imaged. The ultrasound or light energy is reflected back to the ultrasound transducer or fiber optic, respectively. The signal is then transmitted to the proximal end of the device where it is processed to produce an image.

In some embodiments of the current invention, the elongate member has one or more lumens along the longitudinal axis of the elongate member. The lumen(s) can be used to house the actuator mechanism, compliant mechanism, optical fiber and other devices described herein. The lumen(s) can also be used to house wiring which connects the ultrasound transducer(s) and SMA actuator(s) disposed in the distal end of the elongate member to devices located adjacent to the proximal end of the elongate member. These devices include, for example, other components of an ultrasound or OCT imaging system, such as an ultrasound or light source generator, receiver and computer located near the proximal end of the elongate member. In some embodiments, the imaging device of the invention is connected wirelessly to one or more components of the imaging system. The ultrasound imaging device of the invention is optionally configured to provide real-time imaging of the environment at the distal end of the elongate member. Other devices include a signal generator for controlling the activation of the SMA actuators.

The lumen(s) can also be used to flush the distal end of the ultrasound device with fluid. This fluid can improve the ultrasound signal, can be used to flush the area around the IVUS imaging device to ensure that the area is free of debris or bubbles which would interfere with the performance of the ultrasound device, and cool the ultrasound transducer and/or the SMA actuators. In an embodiment with using one or more lumens to flush the distal end of any of the devices described herein, it is desirable to provide a means for the fluid to circulate through the area around the ultrasound transducer, such as another lumen to return the fluid to the proximal end of the elongate member, or an opening in the distal end of the elongate member so that the fluid can escape. Optionally, a fluid pump can be attached to the proximal end of the elongate member to facilitate fluid circulation through the lumen(s). In another embodiment, the distal end of the elongate member contains fluid which is sealed or injected in the distal end and/or a lumen of the elongate member.

In another embodiment, SMA actuators can be used to bend or steer the distal end of the elongate members disclosed herein to allow the user to reduce the distance between the distal end of the device and image target. In the case of intravascular OCT this reduces the artifact caused by blood between the image acquisition device and the vessel wall by bringing the imaging portion of the device closer to the wall itself. Similar to current intravascular ultrasound system (IVUS), local actuators can provide the pull-back motion of the imaging tip, so it can control precisely the pull-back of the distal imaging tip and generate three-dimensional images of the blood vessel.

As discussed above, the angle or orientation of the ultrasound transducer or reflector, or the OCT reflector or prism can determine where the imaging energy is directed. For some applications, these elements direct the energy generally orthogonally from the longitudinal axis of the device. For other applications, these elements can be oriented to direct the imaging energy toward the distal tip of the device, resembling forward looking devices, or toward the proximal end of the device. In another embodiment of the invention, an additional SMA actuator is incorporated into the device to actively move the transducer, reflector or prism and change the imaging plane adaptively. This active angle control can provide side-looking and forward-looking as needed with a single imaging device.

In another embodiment, the IVUS system described herein and the OCT device described herein are combined in a single elongate member to provide both IVUS and OCT imaging in a single, compact device.

Although the embodiments described herein have the imaging devices located in the distal end of the elongate member, one of skill in the art will recognize that the imaging devices can be placed anywhere along the length of the elongate member.

In another embodiment, the imaging devices disclosed herein are integrated into the distal end of a guide wire's rigid section, but proximal to the coil structure that defines the distal tip of a guidewire.

In another embodiment, the imaging devices described herein are combined with one or more therapeutic or interventional devices, for example, but not limited to, devices for stent placement and deployment, balloon angioplasty, directional atherectomy, cardiac ablation, PFO (patent foramen ovule) closure, transvascular re-entry, trans-septal punch, and CTO (chronic total occlusion) crossing.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A side-looking intravascular ultrasound apparatus comprising:
   an elongate member having a proximal end and a distal end, wherein at least a portion of said distal end is at least transparent to ultrasound energy;

an actuator mechanism disposed in said distal end, said actuator mechanism comprising a first anchor, a second anchor, at least one movable element, a first shape memory alloy (SMA) actuator connected to said first anchor and a movable element, and a deformable component connected to said second anchor and at least one movable element, wherein said anchor elements are secured to said elongate member;

wherein said first anchor, said second anchor, said at least one movable element, said first SMA actuator, and said deformable component of said actuator mechanism are disposed along a longitudinal axis that is oriented substantially parallel to a longitudinal axis of said elongate member; and an ultrasound transducer connected to said movable element, said transducer oriented to transmit ultrasound energy through said ultrasound transparent portion of said distal end at an angle of between about 15° to about 165° relative to said longitudinal axis of said elongate member;

wherein said first SMA actuator has an activated and a deactivated state; and wherein said movable element and transducer move in a first direction relative to the elongate member upon activation of said first SMA actuator, wherein said first direction of movement is selected from the group consisting of rotation of the movable element in a direction around an axis that is substantially parallel to said longitudinal axis of said elongate member, longitudinal movement of the movable element substantially parallel to said longitudinal axis of said elongate member, and a combination thereof.

2. The apparatus of claim 1, wherein said deformable component comprises a second SMA actuator;
wherein said second actuator has an activated and a deactivated state; and
wherein activation of said second SMA actuator moves said movable element and transducer relative to the elongate member in a second direction of movement which is counter to said first direction of movement.

3. The apparatus of claim 1, wherein said deformable component is elastic or superelastic;
wherein said deformable component has a relaxed state and a deformed state;
wherein said deformable component is in a relaxed state when said first SMA actuator is deactivated;
wherein said movement of said movable element and transducer in said first direction upon activation of said first SMA actuator deforms said elastic or superelastic deformable component; and
wherein following deactivation of said first SMA actuator, said elastic or superelastic deformable component substantially returns to said relaxed state, said movable element and transducer moving in a second direction of movement which is counter to said first direction of movement.

4. The apparatus of claim 1, wherein said elongate member is a guide wire.

5. The apparatus of claim 1, further comprising:
a lumen traversing the longitudinal axis of the elongate member; and
wires disposed in said lumen to electrically connect said transducer, first SMA actuator and optionally said deformable component to one or more devices at the proximal end of said elongate member.

6. The apparatus of claim 5, wherein said device is an ultrasound signal processor.

7. The apparatus of claim 1, further comprising a second ultrasound transducer connected to said movable element.

8. The apparatus of claim 1, wherein said angle is between about 80° and about 110°.

9. The apparatus of claim 1, wherein the diameter of said distal end of said elongate member is not more than about 0.060 inches.

10. The apparatus of claim 1, further comprising a connecting arm;
said connecting arm connecting said ultrasound transducer to said movable element;
wherein said movable element, connecting arm and transducer move in said first direction relative to the elongate member upon activation of said first SMA actuator.

11. The apparatus of claim 10, wherein said deformable component comprises a second SMA actuator;
wherein said second actuator has an activated and a deactivated state; and
wherein activation of said second SMA actuator moves said movable element, connector and transducer relative to the elongate member in a second direction of movement which is counter to said first direction of movement.

12. The apparatus of claim 10, wherein said deformable component is elastic or superelastic;
wherein said deformable component has a relaxed state and a deformed state;
wherein said deformable component is in a relaxed state when said first SMA actuator is deactivated;
wherein said movement of said movable element, connecting arm and transducer in said first direction upon activation of said first SMA actuator deforms said elastic or superelastic deformable component; and
wherein following deactivation of said first SMA actuator, said elastic or superelastic deformable component substantially returns to said relaxed state, said movable element, connecting arm and transducer moving in a second direction of movement which is counter to said first direction of movement.

13. The apparatus of claim 1, wherein said rotational motion is between about 1 and about 400 degrees, or said longitudinal motion is from about 1 mm to about 20 mm.

14. The apparatus of claim 1, further comprising a second ultrasound transducer connected to a movable element.

15. The apparatus of claim 1, wherein said ultrasound transducer comprises at least two ultrasound crystals.

16. The apparatus of claim 10, wherein said angle is between about 80° and about 110°.

17. The apparatus of claim 10, wherein the diameter of said distal end of said elongate member is not more than about 0.060 inches.

18. A side-looking intravascular ultrasound apparatus comprising:
an elongate member having a proximal end and a distal end, wherein at least a portion of said distal end is transparent to ultrasound energy;
an actuator mechanism disposed in said distal end, said actuator mechanism comprising a first anchor, a second anchor, a movable element, a first SMA actuator connected to said first anchor and said movable element, and a deformable component connected to said second anchor and said movable element, wherein said anchor elements are secured to said elongate member;
wherein said first anchor, said second anchor, said at least one movable element, said first SMA actuator, and said deformable component of said actuator mechanism are disposed along a longitudinal axis that is oriented substantially parallel to a longitudinal axis of said elongate member;

a connecting arm and an ultrasound energy reflector, wherein said connecting arm connects said ultrasound energy reflector to said movable element; and an ultrasound transducer disposed in said distal end of said elongate member;

wherein said ultrasound transducer and said ultrasound energy reflector are oriented to transmit ultrasound energy through said ultrasound transparent portion of said distal end at an angle of between about 15° to about 165° relative to said longitudinal axis of said elongate member;

wherein said first SMA actuator has an activated and a deactivated state; and wherein said movable element, connecting arm, and ultrasound energy reflector move in a first direction relative to the elongate member upon activation of said first SMA actuator, wherein said first direction of movement is selected from the group consisting of rotation of the movable element in a direction around an axis that is substantially parallel to said longitudinal axis of said elongate member, longitudinal movement of the movable element substantially parallel to said longitudinal axis of said elongate member, and a combination thereof.

19. The apparatus of claim 18, wherein said deformable component comprises a second SMA actuator;

wherein said second actuator has an activated and a deactivated state; and wherein activation of said second SMA actuator moves said movable element, connecting arm and reflector relative to the elongate member in a second direction which is counter to said first direction of movement.

20. The apparatus of claim 18, wherein said deformable component is elastic or superelastic;

wherein said deformable component has a relaxed state and a deformed state;

wherein said deformable component is in a relaxed state when said first SMA actuator is deactivated;

wherein said movement of said movable element, connecting arm and reflector in said first direction upon activation of said first SMA actuator deforms said elastic or superelastic deformable component; and wherein following deactivation of said first SMA actuator, said elastic or superelastic deformable component substantially returns to said relaxed state, said movable element, connecting element and reflector moving in a second direction of movement which is counter to said first direction of movement.

21. The apparatus of claim 18, wherein said rotational motion is between about 1 and about 400 degrees, or said longitudinal motion is from about 1 mm to about 20 mm.

22. The apparatus of claim 20, wherein said rotational motion is between about 1 and about 400 degrees, or said longitudinal motion is from about 1 mm to about 20 mm.

23. The apparatus of claim 18, further comprising a second ultrasound energy reflector connected to a movable element.

24. The apparatus of claim 18, wherein said angle is between about 80° and about 110°.

25. The apparatus of claim 18, wherein the diameter of said distal end of said elongate member is not more than about 0.060 inches.

26. A method for visualizing the interior of a patient's vasculature, said method comprising:

inserting the distal end of the apparatus of claim 1 into the vasculature of a patient;

generating an ultrasound signal from said transducer;

generating a cyclical movement of said movable element and ultrasound transducer by alternating the activation and deactivation of said first SMA actuator and optionally said deformable component, such that said movable element and ultrasound transducer are moved in said first and said second direction;

receiving an ultrasonic signal reflected from the interior of the vasculature on said transducer; and producing an image from said reflected signal.

27. A method for visualizing the interior of a patient's vasculature, said method comprising:

inserting the distal end of the apparatus of claim 2 into the vasculature of a patient;

generating an ultrasound signal from said transducer;

generating a cyclical movement of said movable element and ultrasound transducer by alternating the activation of said first SMA actuator and said second SMA actuator, such that said movable element and ultrasound transducer are moved in said first and said second direction;

receiving an ultrasonic signal reflected from the interior of the vasculature on said transducer; and producing an image from said reflected signal.

28. A method for visualizing the interior of a patient's vasculature, said method comprising:

inserting the distal end of the apparatus of claim 10 into the vasculature of a patient;

generating an ultrasound signal from said transducer;

generating a cyclical movement of said movable element, connecting arm and ultrasound transducer by alternating the activation and deactivation of said first SMA actuator and optionally said deformable component, such that said movable element, connecting arm and ultrasound transducer are moved in said first and said second direction;

receiving an ultrasonic signal reflected from the interior of the vasculature on said transducer; and producing an image from said reflected signal.

29. A method for visualizing the interior of a patient's vasculature, said method comprising:

inserting the distal end of the apparatus of claim 11 into the vasculature of a patient;

generating an ultrasound signal from said transducer;

generating a cyclical movement of said movable element, connecting arm and ultrasound transducer by alternating the activation of said first SMA actuator and said second SMA actuator, such that said movable element, connecting arm and ultrasound transducer are moved in said first and said second direction;

receiving an ultrasonic signal reflected from the interior of the vasculature on said transducer; and producing an image from said reflected signal.

30. A method for visualizing the interior of a patient's vasculature, said method comprising:

inserting the distal end of the apparatus of claim 18 into the vasculature of a patient;

generating an ultrasound signal from said transducer;

generating a cyclical movement of said movable element, connecting arm and ultrasound energy reflector by alternating the activation of said first SMA actuator and said second SMA actuator, such that said movable element, connecting arm and ultrasound energy reflector are moved in said first and said second direction;

receiving an ultrasonic signal reflected from the interior of the vasculature on said transducer; and producing an image from said reflected signal.

31. A method for visualizing the interior of a patient's vasculature, said method comprising:

inserting the distal end of the apparatus of claim 19 into the vasculature of a patient;

generating an ultrasound signal from said transducer;

generating a cyclical movement of said movable element, connecting arm and ultrasound energy reflector by alternating the activation of said first SMA actuator and said second SMA actuator, such that said movable element, connecting arm and ultrasound energy reflector are moved in said first and said second direction;

receiving an ultrasonic signal reflected from the interior of the vasculature on said transducer; and producing an image from said reflected signal.

32. A side-looking intravascular ultrasound apparatus comprising:

an elongate member having a proximal end and a distal end, wherein at least a portion of said distal end is transparent to ultrasound energy;

an ultrasound transducer disposed in said distal end; and an actuator mechanism means for providing cyclical motion to said transducer disposed in said distal end;

wherein said transducer is oriented to transmit ultrasound energy through said ultrasound transparent portion of said distal end at an angle of between about 15° to about 165° relative to a longitudinal axis of said elongate member, wherein said cyclical motion comprises movement of said transducer in a first direction relative to the elongate member selected from the group consisting of rotation of the transducer in a direction around an axis that is substantially parallel to said longitudinal axis of said elongate member, longitudinal movement of the transducer substantially parallel to said longitudinal axis of said elongate member, and a combination thereof.

33. The side-looking intravascular ultrasound apparatus of claim 32, wherein said actuator mechanism means comprises a first anchor, a second anchor, a movable element, a first SMA actuator connected to said first anchor and said movable element, and a deformable component connected to said second anchor and said movable element, wherein said anchor elements are secured to said elongate member, wherein said first anchor, said second anchor, said at least one movable element, said first SMA actuator, and said deformable component of said actuator mechanism are disposed along a longitudinal axis that is oriented substantially parallel to a longitudinal axis of said elongate member.

34. An intravascular ultrasound apparatus comprising:

an elongate member having a proximal end and a distal end, wherein at least a portion of said distal end is at least transparent to ultrasound energy;

an ultrasound transducer and actuator mechanism disposed in said distal end, said actuator mechanism comprising a first anchor, a second anchor, at least one movable element, a first SMA actuator connected to said first anchor and a movable element, and a deformable component connected to said second anchor and at least one movable element, wherein said anchor elements are secured to said elongate member, wherein said first anchor, said second anchor, said at least one movable element, said first SMA actuator, and said deformable component of said actuator mechanism are disposed along a longitudinal axis that is oriented substantially parallel to a longitudinal axis of said elongate member, wherein said first SMA actuator has an activated and a deactivated state, and wherein said movable element moves said transducer in a first direction relative to the elongate member upon activation of said first SMA actuator, wherein said first direction is longitudinal movement of the movable element substantially parallel to said longitudinal axis of said elongate member.

* * * * *

UNITED STATES PATENT AND TRADEMARK OFFICE
CERTIFICATE OF CORRECTION

| | | |
|---|---|---|
| PATENT NO. | : 7,658,715 B2 | Page 1 of 1 |
| APPLICATION NO. | : 11/415855 | |
| DATED | : February 9, 2010 | |
| INVENTOR(S) | : Park et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 756 days.

Signed and Sealed this

Thirtieth Day of November, 2010

David J. Kappos
*Director of the United States Patent and Trademark Office*